US008556980B2

(12) United States Patent
Deffenbaugh

(10) Patent No.: US 8,556,980 B2
(45) Date of Patent: Oct. 15, 2013

(54) GLENOID AUGMENT AND ASSOCIATED METHOD

(75) Inventor: Daren Lloyd Deffenbaugh, Winona Lake, IN (US)

(73) Assignee: Depuy Synthes Products, LLC, Raynham, MA (US)

( * ) Notice: Subject to any disclaimer, the term of this patent is extended or adjusted under 35 U.S.C. 154(b) by 21 days.

(21) Appl. No.: 12/971,002

(22) Filed: Dec. 17, 2010

(65) Prior Publication Data

US 2011/0144758 A1 Jun. 16, 2011

Related U.S. Application Data

(62) Division of application No. 10/951,024, filed on Sep. 27, 2004, now Pat. No. 7,892,287.

(51) Int. Cl.
*A61F 2/40* (2006.01)

(52) U.S. Cl.
USPC .................................................. 623/19.11

(58) Field of Classification Search
USPC .......... 623/19.11–19.14, 14.12, 16.11, 18.11, 623/20.11, 20.14, 20.15, 22.21, 18.12, 623/20.12, 20.13, 22.11
See application file for complete search history.

(56) References Cited

U.S. PATENT DOCUMENTS

| | | | |
|---|---|---|---|
| 3,061,977 A | 11/1962 | Schmidt | |
| 3,694,820 A * | 10/1972 | Scales et al. | 623/19.12 |
| 3,837,008 A | 9/1974 | Bahler et al. | |
| 3,855,638 A | 12/1974 | Pilliar | |
| 4,040,130 A | 8/1977 | Laure | |
| 4,042,980 A * | 8/1977 | Swanson et al. | 623/19.13 |
| 4,045,825 A * | 9/1977 | Stroot | 623/19.14 |
| 4,045,826 A * | 9/1977 | Stroot | 623/19.11 |
| 4,106,128 A | 8/1978 | Greenwald et al. | |
| 4,172,296 A | 10/1979 | D'Errico | |
| 4,180,871 A | 1/1980 | Hamas | |
| 4,524,467 A | 6/1985 | DeCarlo, Jr. | |
| 4,550,450 A * | 11/1985 | Kinnett | 623/20.11 |
| D285,968 S * | 9/1986 | Kinnett | D24/155 |

(Continued)

FOREIGN PATENT DOCUMENTS

| | | |
|---|---|---|
| DE | 102006041550 | 11/2007 |
| DE | 102008021110 A1 | 10/2009 |

(Continued)

OTHER PUBLICATIONS

Translation of FR 2 652498A1—Inventor: Michel Columbier, Date of Publ. Oct. 4, 1989.

(Continued)

*Primary Examiner* — Alvin J Stewart

(57) ABSTRACT

A augmented glenoid implant assembly for use in performing shoulder arthroplasty is provided. The augmented glenoid implant assembly is used for cooperation with the glenoid fossa of a scapula. The implant assembly includes a first component for attachment to the scapula. The first component defines a support surface for cooperation with the glenoid fossa, a second surface positioned adjacent a buttress formed in the glenoid fossa and an assembly surface. The implant assembly also includes a second component removably secured to the first component. The second component includes an assembly face of the second component. The assembly surface of the second component is in close approximation to the assembly surface of the first component. The second component further includes an articulating surface opposed to the assembly surface.

4 Claims, 32 Drawing Sheets

(56) References Cited

U.S. PATENT DOCUMENTS

| | | | |
|---|---|---|---|
| 4,693,723 A | 9/1987 | Gabard | |
| 4,695,282 A | 9/1987 | Forte et al. | |
| 4,795,468 A | 1/1989 | Hodorek et al. | |
| 4,865,025 A | 9/1989 | Buzzi et al. | |
| 4,865,605 A | 9/1989 | Dines et al. | |
| 4,919,670 A | 4/1990 | Dale et al. | |
| 4,936,853 A | 6/1990 | Fabian et al. | |
| 4,964,865 A * | 10/1990 | Burkhead et al. | 623/19.11 |
| 4,986,833 A * | 1/1991 | Worland | 623/19.11 |
| 4,987,904 A | 1/1991 | Wilson | |
| 5,030,219 A | 7/1991 | Matsen et al. | |
| 5,032,132 A * | 7/1991 | Matsen et al. | 623/19.11 |
| 5,047,058 A | 9/1991 | Roberts | |
| 5,080,673 A | 1/1992 | Burkhead | |
| 5,108,446 A | 4/1992 | Wagner et al. | |
| 5,150,304 A | 9/1992 | Berchem | |
| 5,197,465 A | 3/1993 | Montgomery | |
| 5,201,882 A | 4/1993 | Paxson | |
| 5,304,181 A | 4/1994 | Caspari et al. | |
| 5,314,479 A | 5/1994 | Rockwood et al. | |
| 5,344,461 A | 9/1994 | Phlipot | |
| 5,358,526 A | 10/1994 | Tornier | |
| 5,370,693 A | 12/1994 | Kelman et al. | |
| 5,387,241 A | 2/1995 | Hayes | |
| 5,437,677 A | 8/1995 | Shearer et al. | |
| 5,458,637 A | 10/1995 | Hayes | |
| 5,474,559 A | 12/1995 | Bertin et al. | |
| 5,486,180 A | 1/1996 | Dietz et al. | |
| 5,489,309 A | 2/1996 | Lackey et al. | |
| 5,489,310 A * | 2/1996 | Mikhail | 623/19.11 |
| 5,496,324 A | 3/1996 | Barnes | |
| 5,507,821 A | 4/1996 | Sennwald et al. | |
| 5,554,158 A | 9/1996 | Vinciguerra et al. | |
| 5,593,441 A | 1/1997 | Lichtenstein et al. | |
| 5,593,448 A | 1/1997 | Dong | |
| 5,601,563 A | 2/1997 | Burke et al. | |
| 5,665,090 A | 9/1997 | Rockwood et al. | |
| 5,702,447 A | 12/1997 | Walch | |
| 5,718,360 A | 2/1998 | Green et al. | |
| 5,723,018 A | 3/1998 | Cyprien et al. | |
| 5,743,915 A | 4/1998 | Bertin et al. | |
| 5,769,855 A | 6/1998 | Bertin et al. | |
| 5,779,710 A | 7/1998 | Matsen | |
| 5,782,924 A | 7/1998 | Johnson | |
| 5,800,551 A | 9/1998 | Williamson et al. | |
| 5,853,415 A | 12/1998 | Bertin et al. | |
| 5,860,981 A | 1/1999 | Bertin et al. | |
| 5,879,401 A | 3/1999 | Besemer et al. | |
| 5,908,424 A | 6/1999 | Bertin et al. | |
| 5,928,285 A * | 7/1999 | Bigliani et al. | 623/19.13 |
| 5,976,145 A | 11/1999 | Kennefick | |
| 6,045,582 A | 4/2000 | Prybyla | |
| 6,096,084 A | 8/2000 | Townley | |
| 6,139,581 A | 10/2000 | Engh et al. | |
| 6,197,062 B1 | 3/2001 | Fenlin | |
| 6,197,063 B1 | 3/2001 | Dews | |
| 6,206,925 B1 | 3/2001 | Tornier | |
| 6,228,119 B1 * | 5/2001 | Ondrla et al. | 623/19.11 |
| 6,228,900 B1 | 5/2001 | Shen et al. | |
| 6,245,074 B1 | 6/2001 | Allard et al. | |
| 6,281,264 B1 | 8/2001 | Salovey et al. | |
| 6,364,910 B1 | 4/2002 | Shultz et al. | |
| 6,368,353 B1 | 4/2002 | Arcand | |
| 6,379,386 B1 * | 4/2002 | Resch et al. | 623/19.13 |
| 6,406,495 B1 | 6/2002 | Schoch | |
| 6,488,715 B1 | 12/2002 | Pope | |
| 6,514,287 B2 * | 2/2003 | Ondrla et al. | 623/19.13 |
| 6,620,197 B2 | 9/2003 | Maroney et al. | |
| 6,673,115 B2 | 1/2004 | Resch et al. | |
| 6,676,705 B1 | 1/2004 | Wolf | |
| 6,679,916 B1 | 1/2004 | Frankle et al. | |
| 6,699,289 B2 * | 3/2004 | Iannotti et al. | 623/19.13 |
| 6,699,290 B1 | 3/2004 | Wack et al. | |
| 6,783,549 B1 * | 8/2004 | Stone et al. | 623/19.14 |
| 6,875,234 B2 * | 4/2005 | Lipman et al. | 623/19.12 |
| 6,893,702 B2 | 5/2005 | Takahashi | |
| 6,896,702 B2 * | 5/2005 | Collazo | 623/20.16 |
| 6,899,736 B1 | 5/2005 | Rauscher et al. | |
| 6,911,047 B2 * | 6/2005 | Rockwood et al. | 623/19.13 |
| 6,942,699 B2 | 9/2005 | Stone et al. | |
| 6,953,478 B2 | 10/2005 | Bouttens | |
| 7,033,396 B2 * | 4/2006 | Tornier | 623/19.11 |
| 7,051,451 B2 | 5/2006 | Augostino et al. | |
| 7,090,677 B2 | 8/2006 | Fallin et al. | |
| 7,160,328 B2 | 1/2007 | Rockwood, Jr. | |
| 7,160,331 B2 | 1/2007 | Cooney et al. | |
| 7,169,184 B2 * | 1/2007 | Dalla Pria | 623/19.12 |
| 7,175,665 B2 | 2/2007 | German et al. | |
| 7,204,854 B2 | 4/2007 | Guederian | |
| 7,329,284 B2 | 2/2008 | Maroney | |
| 7,527,631 B2 | 5/2009 | Maroney et al. | |
| 7,604,665 B2 * | 10/2009 | Iannotti et al. | 623/19.13 |
| 7,608,109 B2 * | 10/2009 | Dalla Pria | 623/19.11 |
| 7,621,961 B2 * | 11/2009 | Stone | 623/19.12 |
| 7,625,408 B2 | 12/2009 | Gupta et al. | |
| 7,753,959 B2 * | 7/2010 | Berelsman et al. | 623/19.11 |
| 7,766,969 B2 | 8/2010 | Justin et al. | |
| 7,892,287 B2 * | 2/2011 | Deffenbaugh | 623/19.11 |
| 7,918,895 B2 | 4/2011 | Isch et al. | |
| 7,922,769 B2 * | 4/2011 | Deffenbaugh et al. | 623/19.11 |
| 7,927,335 B2 * | 4/2011 | Deffenbaugh et al. | 606/87 |
| 8,241,365 B2 | 8/2012 | Williams et al. | |
| 2001/0010636 A1 | 8/2001 | Gotou | |
| 2001/0011192 A1 * | 8/2001 | Ondrla et al. | 623/19.13 |
| 2001/0018589 A1 | 8/2001 | Muller | |
| 2001/0030339 A1 | 10/2001 | Sandhu et al. | |
| 2001/0037153 A1 * | 11/2001 | Rockwood et al. | 623/19.13 |
| 2002/0004685 A1 | 1/2002 | White | |
| 2002/0082702 A1 * | 6/2002 | Resch et al. | 623/19.11 |
| 2002/0095214 A1 * | 7/2002 | Hyde, Jr. | 623/18.12 |
| 2002/0099445 A1 | 7/2002 | Maroney et al. | |
| 2003/0028253 A1 | 2/2003 | Stone et al. | |
| 2003/0045883 A1 | 3/2003 | Chow et al. | |
| 2003/0055507 A1 | 3/2003 | McDevitt et al. | |
| 2003/0065397 A1 | 4/2003 | Hanssen et al. | |
| 2003/0097183 A1 | 5/2003 | Rauscher et al. | |
| 2003/0114933 A1 | 6/2003 | Bouttens et al. | |
| 2003/0125809 A1 * | 7/2003 | Iannotti et al. | 623/19.13 |
| 2003/0149485 A1 | 8/2003 | Tornier | |
| 2003/0187514 A1 | 10/2003 | McMinn | |
| 2004/0064189 A1 | 4/2004 | Maroney et al. | |
| 2004/0122519 A1 * | 6/2004 | Wiley et al. | 623/18.11 |
| 2004/0122520 A1 * | 6/2004 | Lipman et al. | 623/19.12 |
| 2004/0162619 A1 | 8/2004 | Blaylock et al. | |
| 2004/0193277 A1 | 9/2004 | Long et al. | |
| 2004/0193278 A1 | 9/2004 | Maroney et al. | |
| 2004/0220673 A1 | 11/2004 | Pria | |
| 2004/0220674 A1 * | 11/2004 | Pria | 623/19.12 |
| 2004/0230312 A1 | 11/2004 | Hanson et al. | |
| 2004/0236424 A1 | 11/2004 | Berez | |
| 2005/0021148 A1 | 1/2005 | Gibbs | |
| 2005/0049709 A1 * | 3/2005 | Tornier | 623/19.13 |
| 2005/0125068 A1 | 6/2005 | Hozack et al. | |
| 2005/0171613 A1 | 8/2005 | Sartorius et al. | |
| 2005/0261775 A1 * | 11/2005 | Baum et al. | 623/19.12 |
| 2006/0030946 A1 | 2/2006 | Ball et al. | |
| 2006/0069443 A1 | 3/2006 | Deffenbaugh et al. | |
| 2006/0069444 A1 | 3/2006 | Deffenbaugh | 623/19.11 |
| 2006/0074353 A1 | 4/2006 | Deffenbaugh et al. | |
| 2006/0074430 A1 | 4/2006 | Deffenbaugh et al. | |
| 2006/0079963 A1 * | 4/2006 | Hansen | 623/19.11 |
| 2006/0100498 A1 | 5/2006 | Boyce | |
| 2006/0100714 A1 * | 5/2006 | Ensign | 623/20.16 |
| 2006/0111787 A1 * | 5/2006 | Bailie et al. | 623/19.13 |
| 2006/0149387 A1 * | 7/2006 | Smith et al. | 623/19.11 |
| 2006/0149388 A1 * | 7/2006 | Smith et al. | 623/19.11 |
| 2006/0161260 A1 | 7/2006 | Thomas et al. | |
| 2007/0055380 A1 | 3/2007 | Berelsman | |
| 2007/0142917 A1 | 6/2007 | Roche | |
| 2007/0179624 A1 * | 8/2007 | Stone et al. | 623/19.13 |
| 2007/0219637 A1 * | 9/2007 | Berelsman et al. | 623/19.11 |
| 2007/0219638 A1 | 9/2007 | Jones et al. | |
| 2007/0225817 A1 | 9/2007 | Reubelt et al. | |
| 2008/0046091 A1 | 2/2008 | Weiss | |

(56) References Cited

U.S. PATENT DOCUMENTS

| | | |
|---|---|---|
| 2008/0140209 A1 | 6/2008 | Iannotti |
| 2008/0208348 A1 | 8/2008 | Fitz |
| 2008/0234820 A1 | 9/2008 | Felt et al. |
| 2009/0125113 A1* | 5/2009 | Guederian et al. ......... 623/19.11 |
| 2009/0143865 A1 | 6/2009 | Hassler et al. |
| 2009/0204225 A1 | 8/2009 | Meridew et al. |
| 2009/0281630 A1 | 11/2009 | Delince et al. |
| 2009/0292364 A1* | 11/2009 | Linares ...................... 623/19.13 |
| 2009/0312839 A1 | 12/2009 | Scheker et al. |
| 2010/0049327 A1* | 2/2010 | Isch et al. ................... 623/19.12 |
| 2011/0035013 A1 | 2/2011 | Winslow |
| 2011/0106267 A1 | 5/2011 | Grant |

FOREIGN PATENT DOCUMENTS

| | | |
|---|---|---|
| EP | 0103246 A1 | 3/1984 |
| EP | 339530 A1 | 11/1989 |
| EP | 0339530 A2 | 11/1989 |
| EP | 0329854 B1 | 11/1992 |
| EP | 0538895 A2 | 4/1993 |
| EP | 0538895 A3 | 4/1993 |
| EP | 581667 A1 | 2/1994 |
| EP | 776636 A1 | 6/1997 |
| EP | 0903127 B1 | 3/1999 |
| EP | 1013246 A1 | 6/2000 |
| EP | 776636 B1 | 9/2000 |
| EP | 1064890 A1 | 1/2001 |
| EP | 1013246 B1 | 10/2003 |
| EP | 1402853 A2 | 3/2004 |
| EP | 1064890 B1 | 9/2005 |
| EP | 1402853 A3 | 3/2006 |
| EP | 1639966 A1 | 3/2006 |
| EP | 1639967 A1 | 3/2006 |
| EP | 1639966 B1 | 9/2007 |
| EP | 1902689 A1 | 3/2008 |
| EP | 1639967 B1 | 7/2008 |
| EP | 1402853 B1 | 5/2010 |
| EP | 1902689 B1 | 11/2011 |
| FR | 1064890 A | 5/1954 |
| FR | 2578162 A1 | 9/1986 |
| FR | 2579454 A1 | 10/1986 |
| FR | 2652498 A1 | 4/1991 |
| FR | 2683142 A1 | 5/1993 |
| FR | 2695313 A1 | 3/1994 |
| FR | 2704747 A1 | 11/1994 |
| FR | 2755847 A1 | 5/1998 |
| FR | 2776506 A1 | 10/1999 |
| FR | 2825263 A1 | 12/2002 |
| GB | 2297257 A | 7/1996 |
| WO | WO 01/34040 A1 | 5/2001 |
| WO | WO 02/067821 A2 | 9/2002 |
| WO | WO 02/067821 A3 | 9/2002 |
| WO | WO 03/005933 A2 | 1/2003 |
| WO | WO 03/005933 A3 | 1/2003 |
| WO | WO 03/030770 A2 | 10/2003 |
| WO | WO 2007096741 A2 | 8/2007 |
| WO | WO 2007096741 A3 | 12/2007 |
| WO | WO 2011098890 A1 | 8/2011 |

OTHER PUBLICATIONS

Translation of EP0339530—Inventor: Hans Grundel; Date of Publ. Nov. 2, 1989.

Print out from espacenet of FR2704747 (A1)—Inventor: Didier Capon etal; Date of Pub. Nov. 10, 1994.

Print out from esapcenet of FR2776506(A1)—Inventor: Katz Denis etal; Date of Pub. Oct. 1, 1999.

EPO SR for DEP6138 (EP09178360) Dated May 12, 2010 (7 pages).

Biomet Biomodular Low Profile Modular Glenoid, Biomet Corporation, One Page, Available at Least as Early as Dec. 17, 2010.

Biomet Biangular Standard Metal Backed Glenoid, Biomet Corporation, One Page, 1996.

Kirschner Integrated Shoulder System for Hemi & Total Shoulder Arthroplasty, Kirschner Medical Corporation, Two Pages, Available at Least as Early as Dec. 17, 2010.

The Cofield Total Shoulder System, Smith & Nephew Richards, Inc., Two Pages, Available at Least as Early as Dec. 17, 2010.

European SR Completed Sep. 10, 1999, Mailed Sep. 17, 1999.

PCT Search Report for PCT/US2011/061347, Dated Feb. 9, 2012, 11 pages.

PCT Search Report for PCT/US2011/061357, Dated Feb. 3, 2012, 18 pages.

* cited by examiner

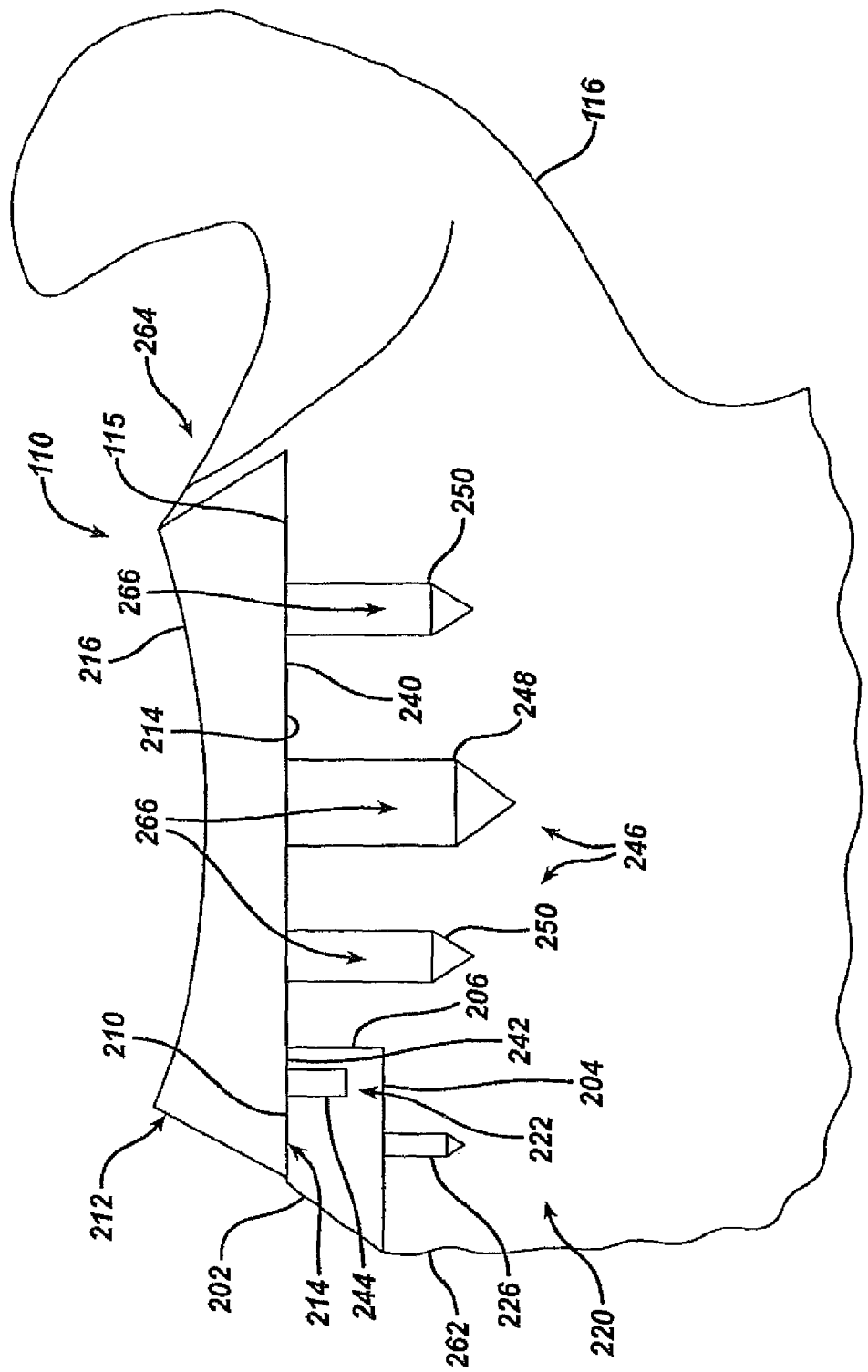

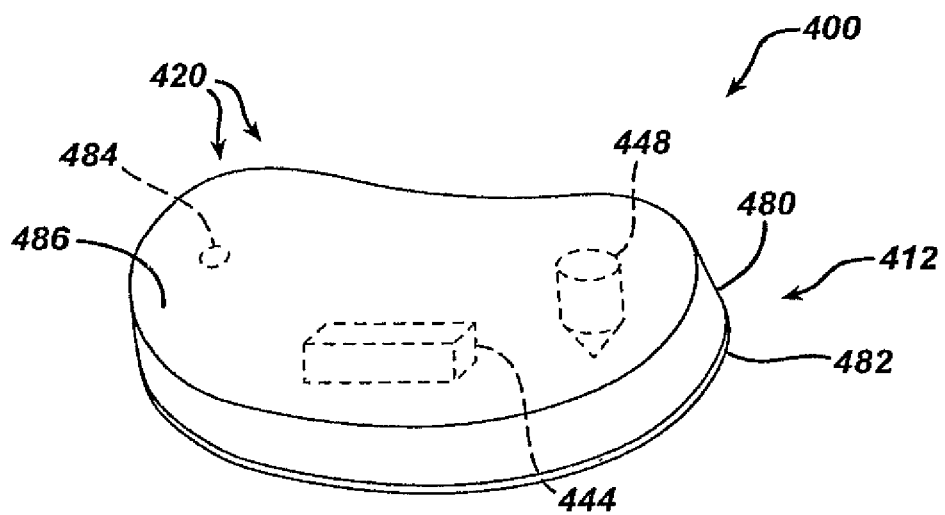
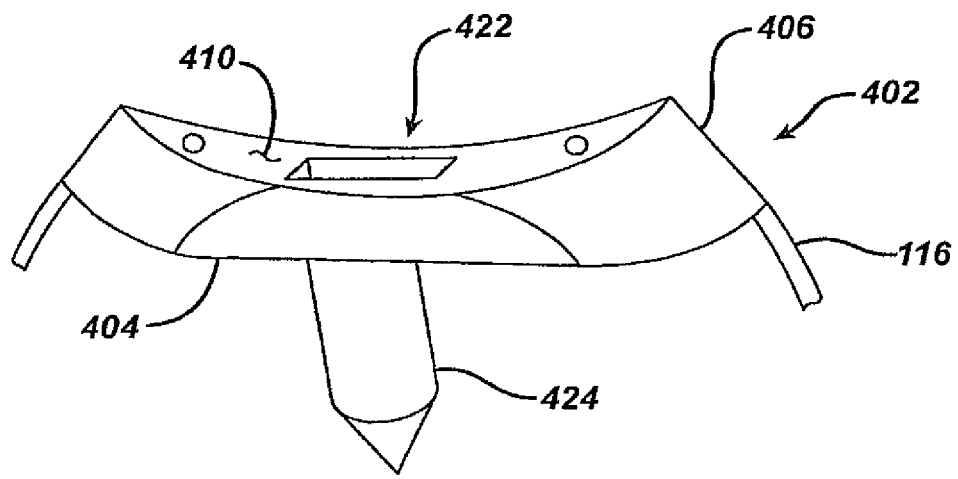
FIG. 18D

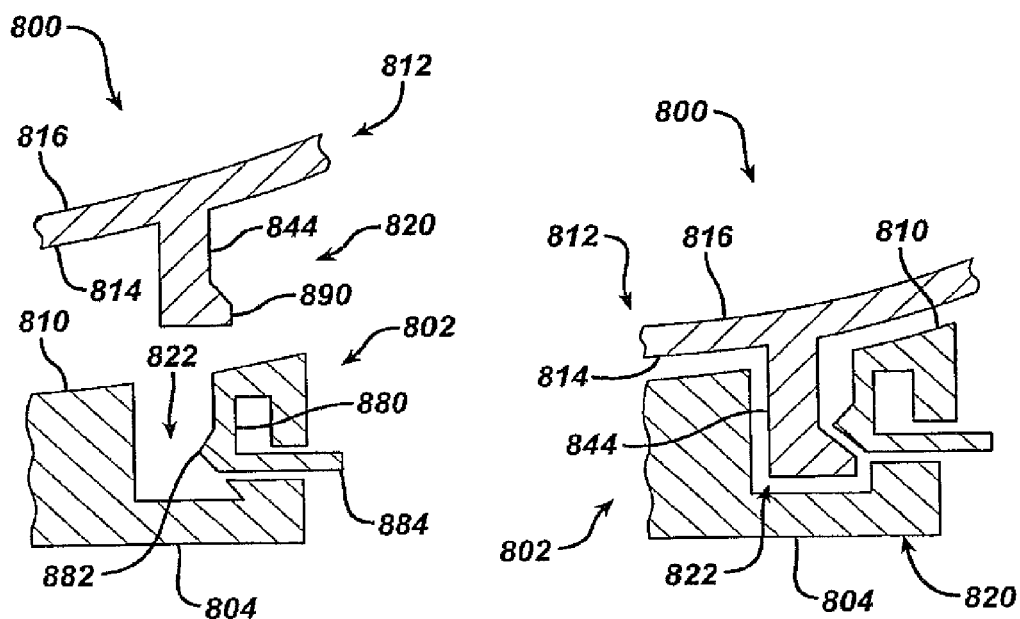

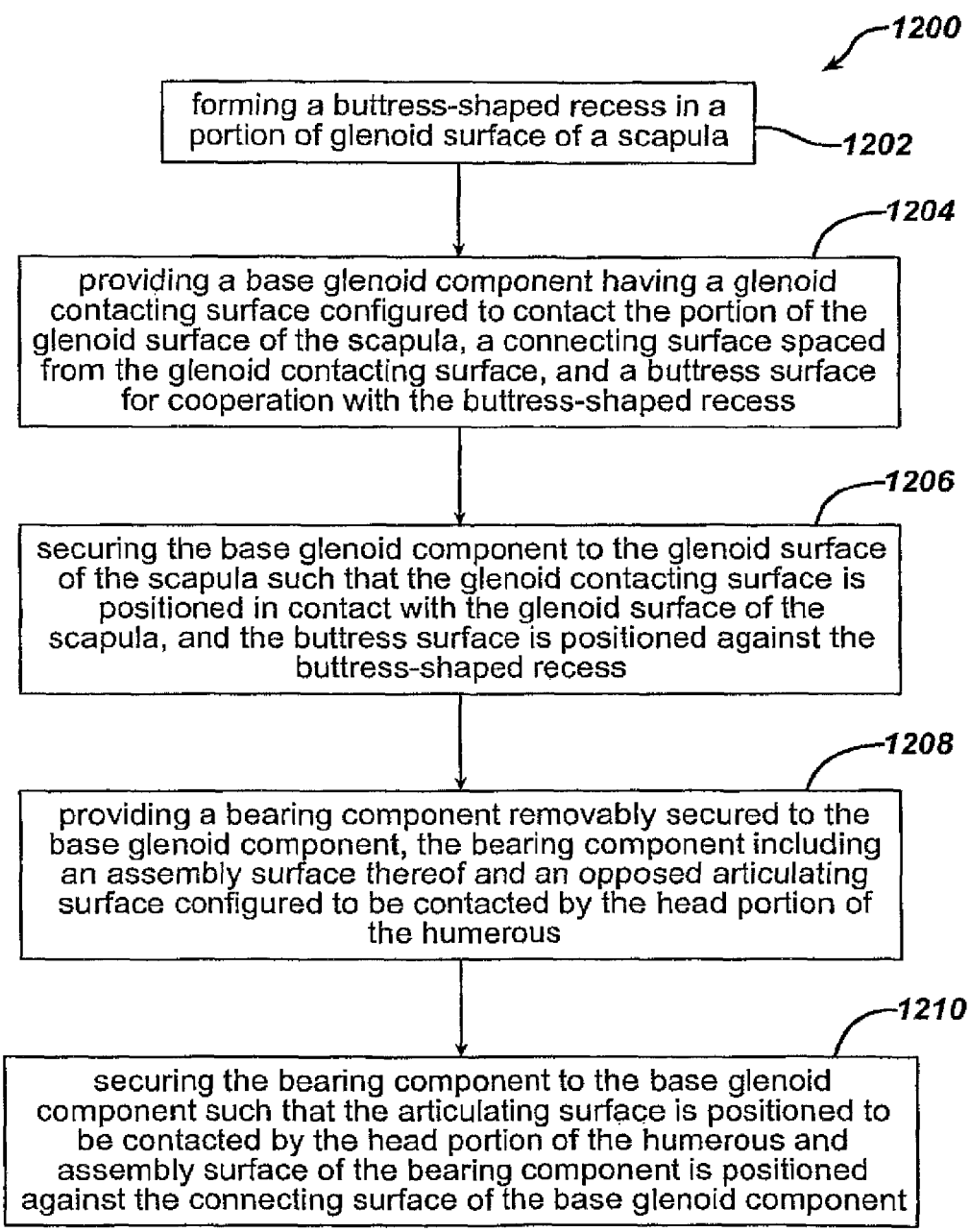

GLENOID AUGMENT AND ASSOCIATED METHOD

CROSS-REFERENCE TO RELATED APPLICATIONS

This is a divisional application of patent application Ser. No. 10/951,024, filed Sep. 27, 2004, now U.S. Pat. No. 7,892,287 entitled "GLENOID AUGMENT AND ASSOCIATED METHOD", which is incorporated by reference herein in its entirety. Cross-reference is made to the following applications: U.S. patent application Ser. No. 10/951,023 entitled "EXTENDED ARTICULATION PROSTHESIS ADAPTOR AND ASSOCIATED METHOD", U.S. Pat. No. 7,927,335 entitled "INSTRUMENT FOR PREPARING AN IMPLANT SUPPORT SURFACE AND ASSOCIATED METHOD", U.S. Pat. No. 7,922,769 entitled "MODULAR GLENOID PROSTHESIS AND ASSOCIATED METHOD", and U.S. patent application Ser. No. 10/951,022 entitled "GLENOID INSTRUMENTATION AND ASSOCIATED METHOD," which are incorporated herein by reference in their entireties.

TECHNICAL FIELD OF THE INVENTION

The present invention relates generally to the field of orthopaedics, and more particularly, to an implant for use in arthroplasty.

BACKGROUND OF THE INVENTION

During the lifetime of a patient, it may be necessary to perform a total shoulder replacement procedure on the patient as a result of, for example, disease or trauma. In a total shoulder replacement procedure, a humeral component having a head portion is utilized to replace the natural head portion of the arm bone or humerus. The humeral component typically has an elongated intramedullary stem which is utilized to secure the humeral component to the patient's humerus. In such a total shoulder replacement procedure, the natural glenoid surface of the scapula is resurfaced or otherwise replaced with a glenoid component that provides a bearing surface for the head portion of the humeral component.

As alluded to above, the need for a shoulder replacement procedure may be created by the presence of any one of a number of conditions. One such condition is the deterioration of the patient's scapula in the area proximate to the glenoid surface as a result of, for example, glenohumeral arthritis. In such a condition, the erosion of the patient's scapula is generally observed posteriorly on the glenoid surface. Such erosion of the scapula renders treatment difficult, if not impossible, with a conventional glenoid prosthesis.

In order to treat a condition in which a portion of the scapula has been eroded, a number of glenoid prostheses have heretofore been designed. Such glenoid prostheses, known generally as augmented glenoid prostheses, have a posterior edge that is thicker than the corresponding anterior edge.

In FIG. 1, a heretofore-designed augmented glenoid component 100 is shown. The glenoid component 100 has a metallic backing component 102 and plastic insert 104. The thickness of the metallic backing component 102 gradually increases from an anterior edge 106 to a posterior edge 108 thereof thereby creating a relatively smooth, arcuate-shaped medial surface 110 from which a number of posts or pegs 112 extend.

The design of the augmented glenoid component 100, however, has a number of associated drawbacks. For example, the relatively smooth, arcuate-shaped medial surface 110 may over time lead to loosening of the augmented glenoid component 100, thereby potentially necessitating additional surgical procedures to replace or reseat the component 100. Further, due to the configuration of the medial surface 110, a relatively high shear load is created along the implant-to-bone interface when the component 100 is implanted. The presence of a high shear load along the implant-to-bone interface tends to also cause loosening of the component 100 over a period of time. Post-operative loosening is the largest cause of failures of implanted glenoid components.

In FIG. 2 another heretofore-designed augmented glenoid component 100A is shown. The glenoid component 100A has a single component plastic body 102A. The thickness of the plastic body 102A gradually increases from an anterior edge 106A to a posterior edge 108A thereof thereby creating a relatively smooth, arcuate-shaped medial surface 110A from which a number of posts or pegs 112A extend. The design of this augmented glenoid component 100A, however, suffers from at least the same drawbacks as the glenoid component 100.

In FIG. 3 another heretofore-designed augmented glenoid component 100B is shown. The glenoid component 100B also has a single component plastic body 102B. The thickness of the plastic body 102B gradually increases from an anterior edge 106B to a posterior edge 108B thereof thereby creating a relatively smooth medial surface 110B from which a keel 114B extends. The design of this augmented glenoid component 100B, however, suffers from at least the same drawbacks as the glenoid components 100 and 100A.

What is needed therefore is an augmented glenoid component that overcomes one or more of the above-mentioned drawbacks. What is further needed is an augmented glenoid component that is less susceptible to postoperative loosening relative to heretofore designed glenoid components.

Attempts have been made in the prior art to provide for a glenoid implant that accommodates posterior erosion. In fact, a device has been designed for augmented glenoid component to accommodate posterior erosion. This attempt at finding a glenoid component to accommodate erosion has provided for generally compressive load and minimize the shear load earlier prior art devices. This device is described in U.S. Pat. No. 6,699,289 to Iannotti et al incorporated herein by reference to its entirety.

Referring now to FIG. 4, a scapula 116 is shown with posterior wear 118. Glenoid component 120 as shown in phantom includes an articulating surface 122, which is symmetrically positioned with respect to the scapula 116. Thus, shown in FIG. 4, the glenoid component 120 is required to be thicker or higher at the portion of the scapula 116 with the posterior defect 118. As shown in FIG. 4, the load factor 124 for the glenoid component 120 is in a different orientation than the load factor 126 normal to the worn scapula 116. Thus, the glenoid component 120 positioned on the scapula 116 includes a force vector 128 that is in shear and that my cause loosening of the glenoid component.

Referring now to FIG. 5, the scapula 116 may be prepared by a buttress or step 130 such that there are two support surfaces 132 and 134 formed on the glenoid fossa of the scapula 116. Preparation of the glenoid cavity is shown in U.S. Pat. No. 6,699,289 to Iannotti et al which is hereby incorporated herein by reference to its entirety. Referring now to FIG. 6, support load vectors 136 are shown parallel load force vectors 138 of the glenoid component 140.

The device of Iannotti provides for and improvement of the load distribution placed upon the glenoid component. This device provides generally for a one piece glenoid component, which is optimum for one particular posterior erosion pattern. A need remains for a posterior augmented glenoid component that may accommodate a wide variety of posterior erosion conditions that may minimize the quantity and types of components necessary to provide for a wide variety of patient needs.

SUMMARY OF THE INVENTION

According to the present invention, a modular posterior augmented glenoid system is provided. The system includes a buttress, which is separate from an articulating component. A buttress may be made of any suitable, durable material and may, for example, made of a metal. The articulating component may be unitary or have two parts and may include a metal backing and a polyethylene articulating component. The buttress may be secured for fixation to the bone. For example, the buttress may include openings to cooperate with screws for fixing the buttress to the bone. The metal backed or polyethylene bearing component may be have a bone cement fixation element as well as an interlocking element fixed to the buttress. The modular glenoid system of the present invention has the potential to adapt for various types of defects and size combinations. The buttress can be configured to permit use of currently available glenoid articulating components to treat posterior erosion.

The modular posterior augmented glenoid system of the present invention may utilize a set of specific reamers to mill a step into the glenoid fossa matched to specific categories of posterior defects. Each depth created by the milling operation may have a corresponding buttress that is secured to the bone below the coracoid and the auxiliary border of the scapular blade.

The buttress may include a keel to help align and support the implant. The articulating component may have two or more distinct fixation mechanisms. The buttress can also have a feature that permits the use of currently commercially available primary glenoids, for example, the global glenoid offered by DePuy Orthopaedics, Warsaw, Ind. in the restoration of normal shoulder function. The feature of the glenoid would have a mechanism to lock the component to the metal buttress. The fixation mechanism for rigid attachment to the buttress can be configured for cemented or cementless fixation to the remaining support bone. If the articulating component is metal backed, the rigid fixation of the metal backing and the metal buttress can be accomplished with screws, snap lock, or other fixation means. The bone fixation can be made with a cemented peg, with porocoat, or by some other means. In the poly-articulating components the rigid fixation can be from snap lock or some other inteference means, and the bone fixation can be Anchor peg, cement peg, keel, or some other means.

According to one embodiment of the present invention, there is provided an augmented glenoid implant assembly for cooperation with the glenoid fossa of a scapula. The implant assembly includes a first component for attachment to the scapula. The first component defines a support surface for cooperation with the glenoid fossa, a second surface positioned adjacent a buttress formed in the glenoid fossa and an assembly surface. The implant assembly also includes a second component removably secured to the first component. The second component includes an assembly face of the second component. The assembly surface of the second component is in close approximation to the assembly surface of the first component. The second component further includes an articulating surface opposed to the assembly surface.

According to another embodiment of the present invention there is provided an augmented glenoid implant assembly. The augmented glenoid implant assembly includes a first component for attachment to the glenoid fossa. The first component defines a support surface for cooperation with the glenoid fossa and an assembly surface. The first component extends only over a portion of the glenoid fossa. The augmented glenoid implant assembly also includes a second component removably secured to the first component. The second component includes an assembly face of the second component. The assembly face of the second component is in close approximation to the assembly surface of the first component. The second component further includes an articulating surface opposed to the assembly surface.

According to a further embodiment of the present invention, there is provided a method of performing shoulder arthroplasty. The method includes the steps of forming a buttress-shaped recess in a portion of glenoid surface of a scapula and providing a base glenoid component. The base glenoid component has a glenoid contacting surface configured to contact the portion of the glenoid surface of the scapula and a connecting surface spaced from the glenoid contacting surface. The base glenoid component also includes a buttress surface for cooperation with the buttress-shaped recess. The method also includes the step of securing the base glenoid component to the glenoid surface of the scapula such that the glenoid contacting surface is positioned in contact with the glenoid surface of the scapula and the buttress surface is positioned against the buttress-shaped recess. The method further includes the step of providing a bearing component removably secured to the base glenoid component. The bearing component includes an assembly surface and an opposed articulating surface configured to be contacted by the head portion of the humerus. The method further includes the step of securing the bearing component to the base glenoid component such that the articulating surface is positioned to be contacted by the head portion of the humerus and assembly surface of the bearing component is positioned against the connecting surface of the base glenoid component.

The technical advantages of the present invention include the ability of the present invention to provide for prostheses support for a glenoid with a posterior defect. For example, according to one aspect of the present invention, an augmented glenoid assembly is provided. The implant assembly cooperates with the glenoid fossa of a scapula. The implant assembly includes a first component for attachment to the scapula. The first component defines the support surface for cooperation with a glenoid fossa and a second surface in positioning adjacent a buttress formed in the fossa and in assembly surface. The implant assembly further includes a second component removably secured to the second component. The first component provides support for the glenoid with the posterior defect. Thus the present invention provides for a prosthesis having support for a glenoid with a posterior defect.

The technical advantages to the present invention further include the ability of the prosthesis of the present invention to re-establish normal glenoid version or orientation. For example, according to one aspect of the present invention, an augmented glenoid implant assembly is provided for cooperation with a glenoid fossa of the scapula. The implant assembly includes a first component for attachment to the scapula and a second component removably secured to the first component. The second component includes an assembly face thereof. The second component further includes an articulating surface opposed to the assembly surface. The assembly and the articulating surface are positioned such that normal glenoid version is re-established. Thus, the present invention provides for the re-establishment of a normal glenoid version.

The technical advantages of the present invention further include the ability of the prosthesis of the present invention to reduce loosening of the implant by matching the strain pattern of the glenoid to the implant or by providing an implant which experiences no shear force, and its normal force to the natural glenoid. For example and according to one aspect of the present invention, augmented glenoid assembly provided including a first component for attachment to the glenoid fossa. The first component defines a support surface and extends over a portion of the glenoid fossa. The first component has an assembly surface in alignment with the strain pattern to provide for no shear forces as does the support surface of the first component. Thus, the present invention provides for the reduction of loosening of the implant by providing a normal strain pattern and by eliminating the shear force.

Technical advantages of the present invention further include the ability of the glenoid assembly of the present invention to provide for modularity or for the combination of components to provide for a large variety of combinations with a smaller number of components. Such modularity provides for lower costs, reduced inventory, and greater offerings of combinations and better fit for patients. For example, according to another aspect of the present invention, an augmented glenoid assembly provides for cooperation with the glenoid fossa of the scapula. The implant assembly includes a first component for attachment to the scapula and a second component removably secured to the first component. Thus, the present invention provides for modularity or the combination of components to provide for greater flexibility and more offerings for the patient.

The technical advantages of the present invention also include the ability of the glenoid assembly of the present invention to include a glenoid bearing that may be used without a posterior defect. The present invention provides for use with a normal standard glenoid component. For example, according to another aspect of the present invention, an augmented glenoid assembly is provided for cooperation with the glenoid fossa of the scapula. The implant assembly includes a first component for attachment to the scapula and a second component removably secured to the first component. The first component extends over a portion of the glenoid fossa. The first component thus, may be used to accommodate the posterior defect. The augmented glenoid assembly also includes a second component that is positioned over substantially all the glenoid fossa. This second component may be identical to the glenoid component used for a natural glenoid without an extensive wear or posterior defect. Thus, the present invention provides for a glenoid bearing that may be used without a posterior defect.

Other technical advantages of the present invention will be readily apparent to one skilled in the art from the following figures, descriptions and claims.

BRIEF DESCRIPTION OF THE DRAWINGS

FIG. 17 is an plan view partially in cross section showing the modular augmented glenoid assembly of FIG. 12 in position on a glenoid;

FIG. 18D is an exploded perspective view of the modular augmented glenoid assembly of FIG. 18B;

FIG. 25 is an exploded partial plan view of a further embodiment of the present invention in the form of a modular augmented glenoid assembly including a locking feature in the form of a cavity and a protrusion;

FIG. 26 is a partial plan view of the modular augmented glenoid assembly of FIG. 25;

FIG. 36 is a flow chart for a method of performing shoulder arthroplasty in accordance to yet another embodiment of the present invention.

Corresponding reference characters indicate corresponding parts throughout the several views. Like reference characters tend to indicate like parts throughout the several views.

DETAILED DESCRIPTION OF THE INVENTION

Figure 1:
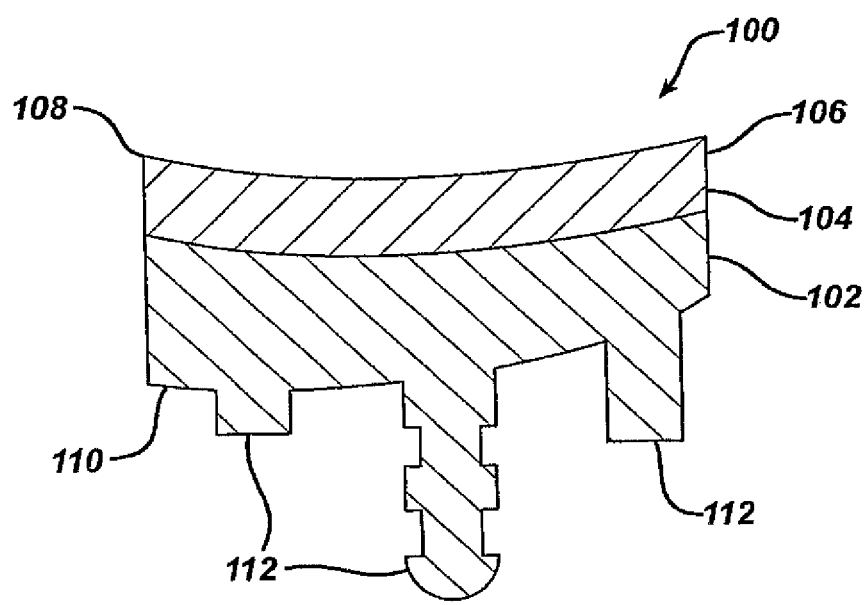
FIG. 1 is a side sectional view of a prior art augmented glenoid component.
Figure 2:
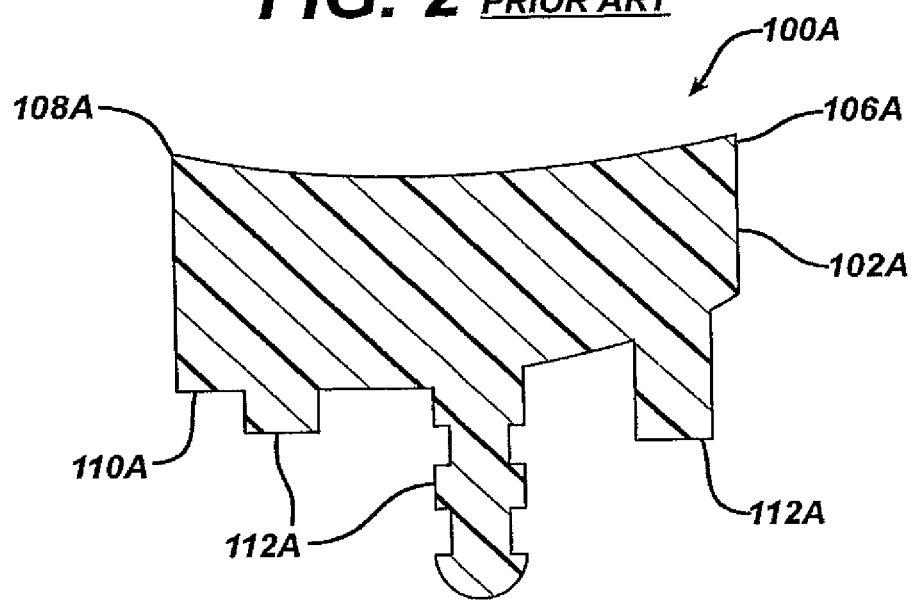
FIG. 2 is a side sectional view of another prior art augmented glenoid component.
Figure 3:
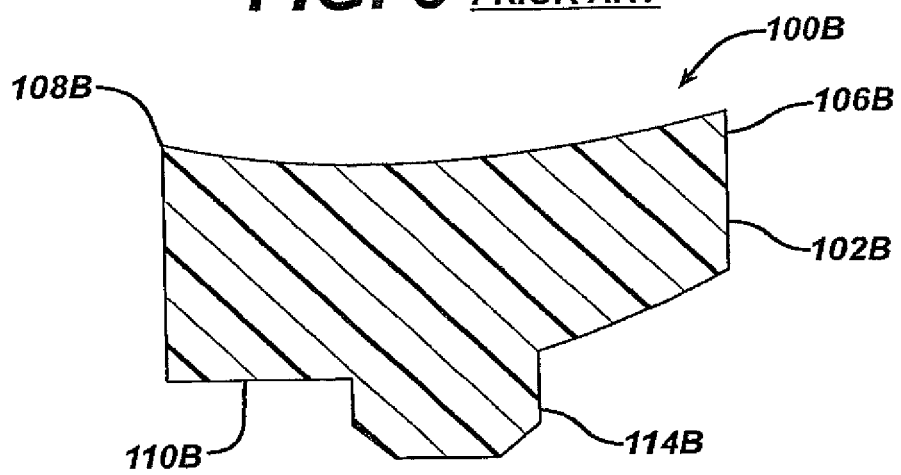
FIG. 3 is a side sectional view of another prior art augmented glenoid component.
Figure 4:
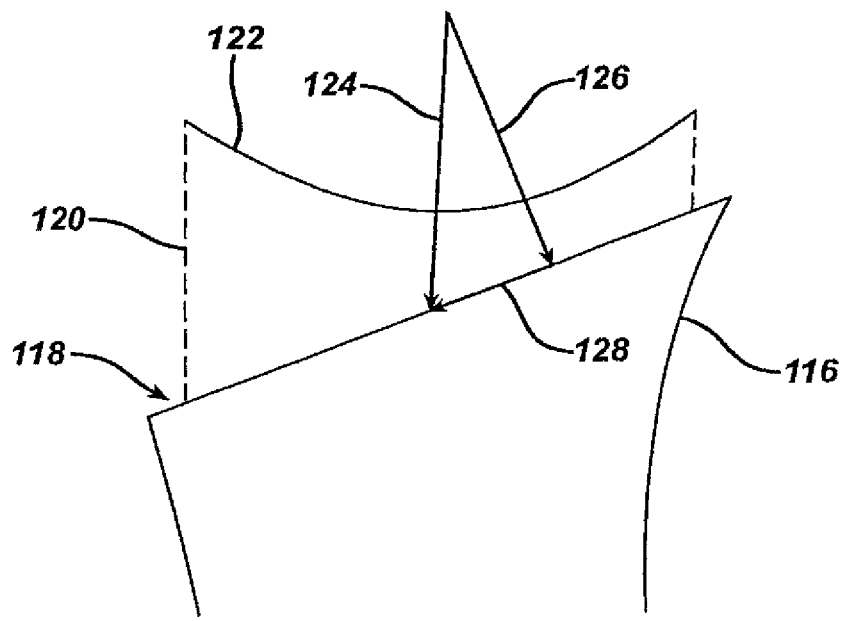
FIG. 4 is a side view of a prior art posterior augmented glenoid component in position on a glenoid, showing a undesirable shearing force vector.
Figure 5:
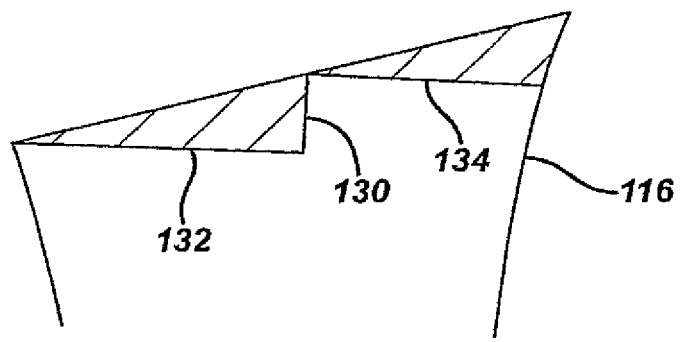
FIG. 5 is a side view of a glenoid cavity prepared for a stepped posterior augmented glenoid component.
Figure 6:
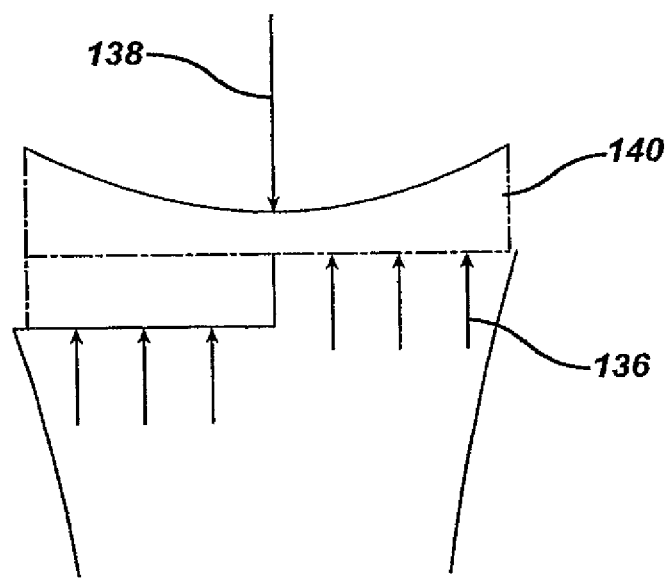
FIG. 6 is a side sectional view of the glenoid cavity prepared for a stepped posterior augmented glenoid component showing the preferred normal force vectors.
Figure 7:
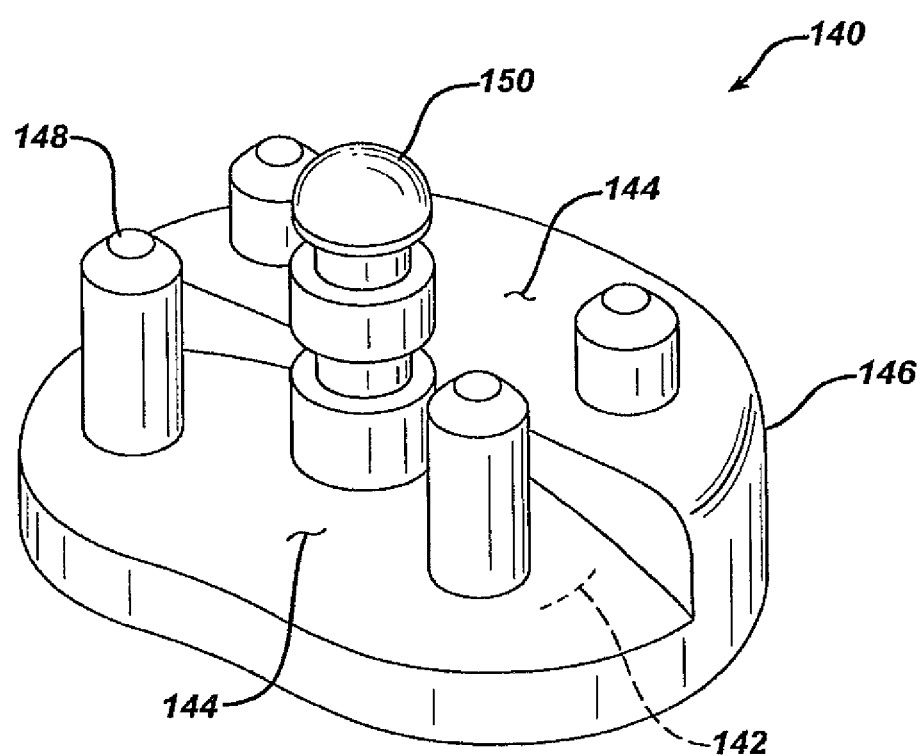
FIG. 7 is a perspective view showing a unitary prior art augmented glenoid component.
Figure 8:
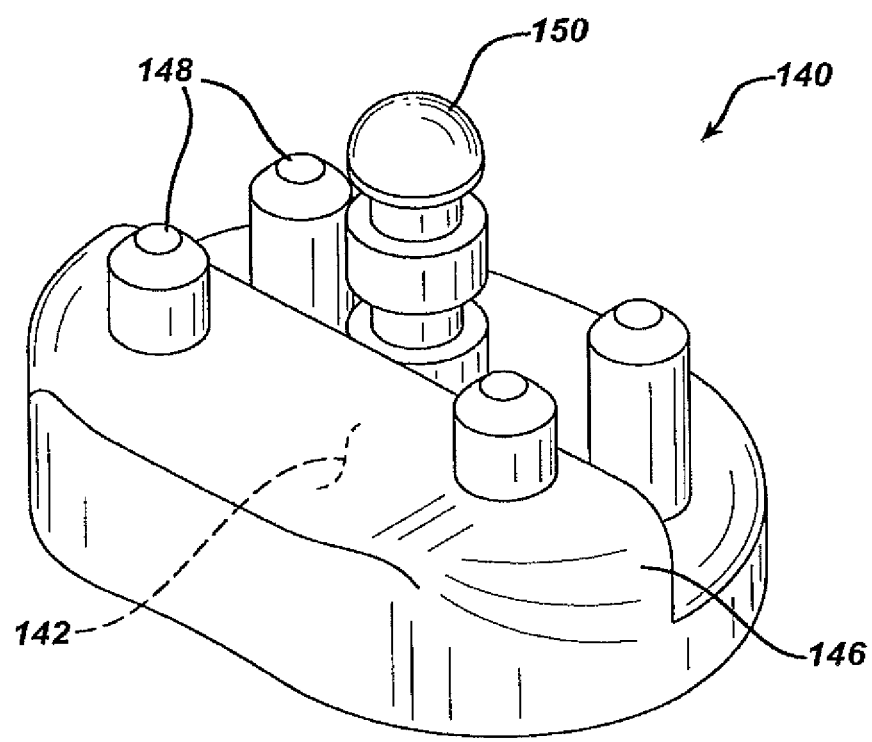
FIG. 8 is another perspective view of the augmented glenoid component of FIG. 7.
Figure 9:
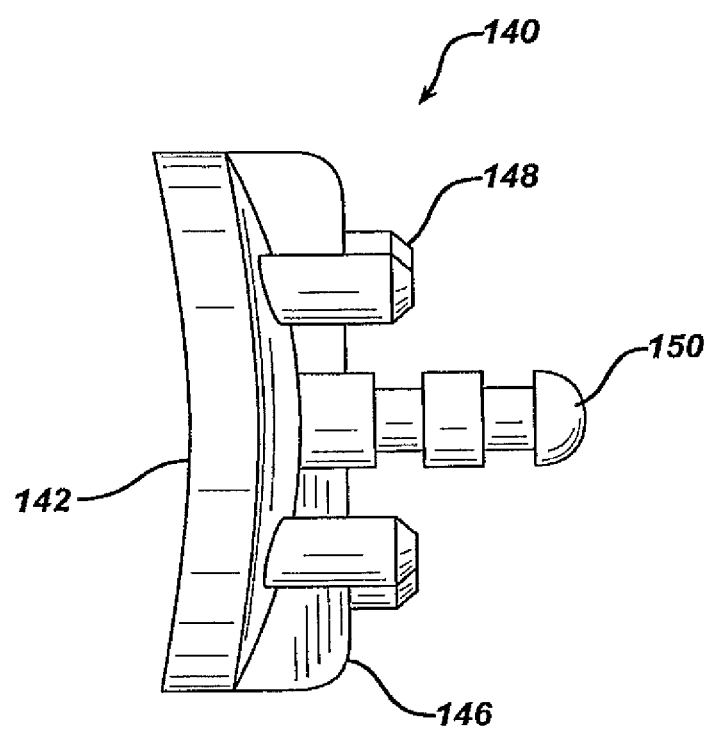
FIG. 9 is an end view of the augmented glenoid component of FIG. 7.
Figure 10:
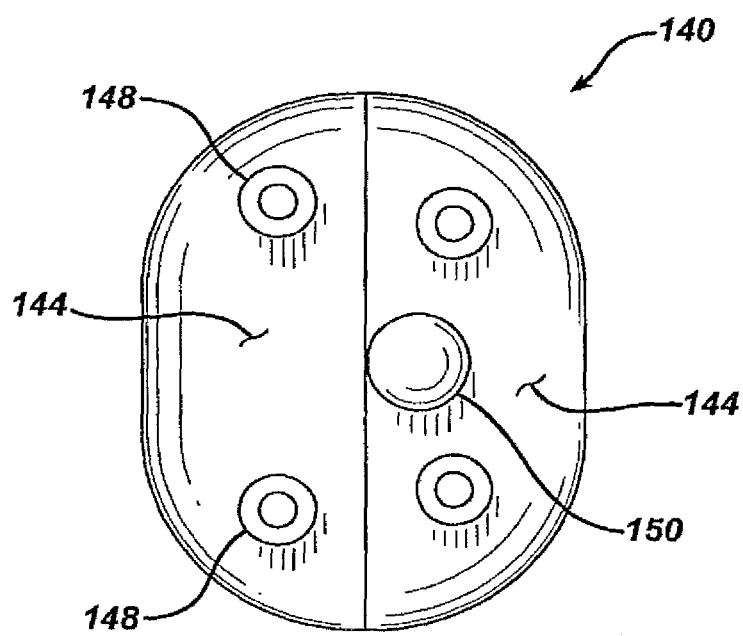
FIG. 10 is an bottom view of the augmented glenoid component of FIG. 7.
Figure 11:
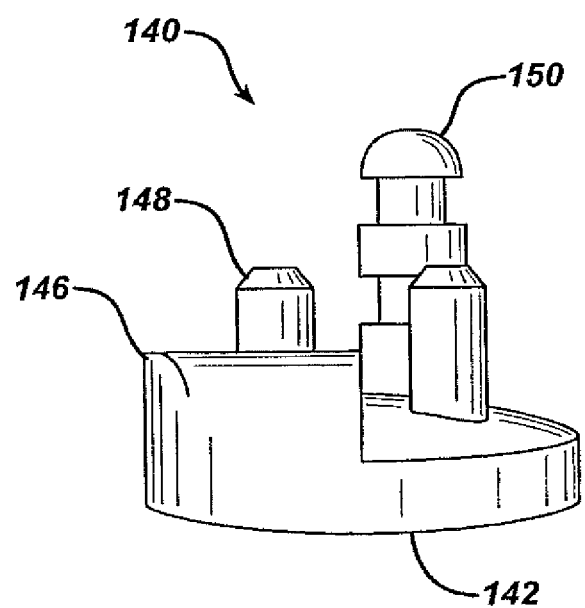
FIG. 11 is a side view of the augmented glenoid component of FIG. 7.

Embodiments of the present invention and the advantages thereof are best understood by referring to the following descriptions and drawings, wherein like numerals are used for like and corresponding parts of the drawings.

Referring now to FIG. 7-11, a stepped glenoid component 140 is shown in. The glenoid component 140 includes an articulating surface 142 as well as opposed mounting surfaces 144. The glenoid component 140 may include a posterior augment 146 as well as anchoring pegs 148 and a central peg 150.

Figure 12:
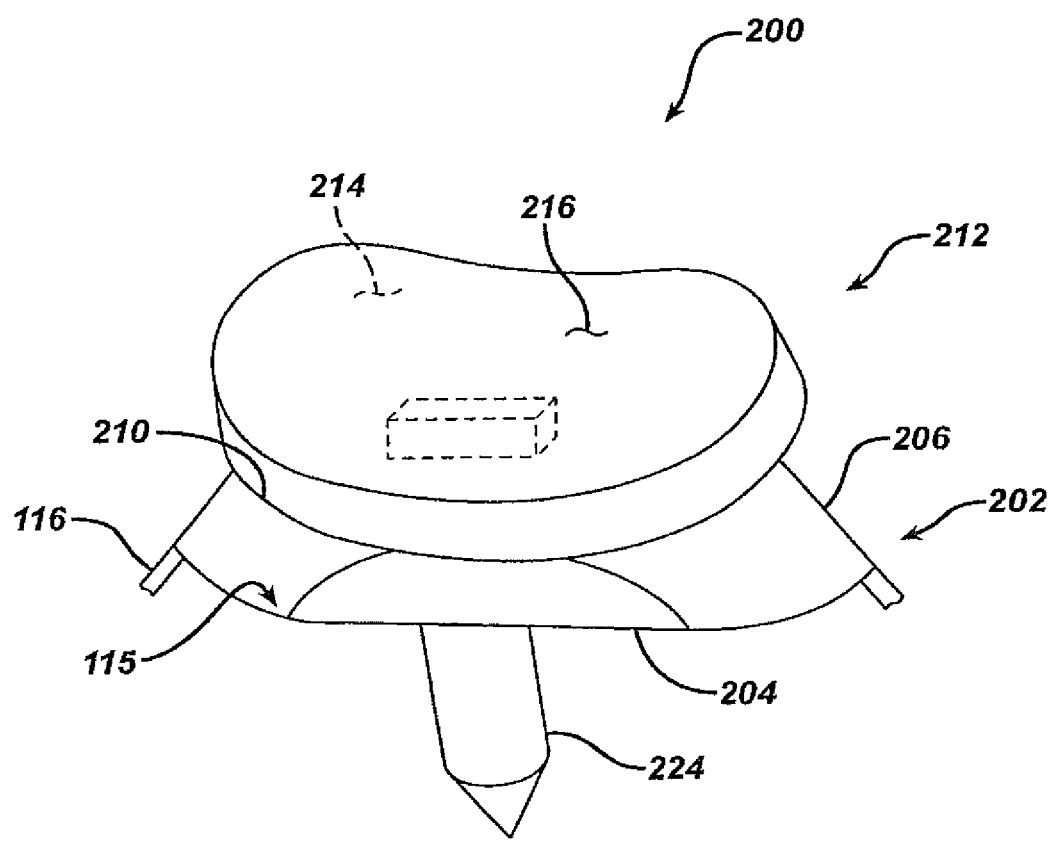
FIG. 12 is a perspective view of another embodiment of a modular augmented glenoid assembly of the present invention.
Figure 13:
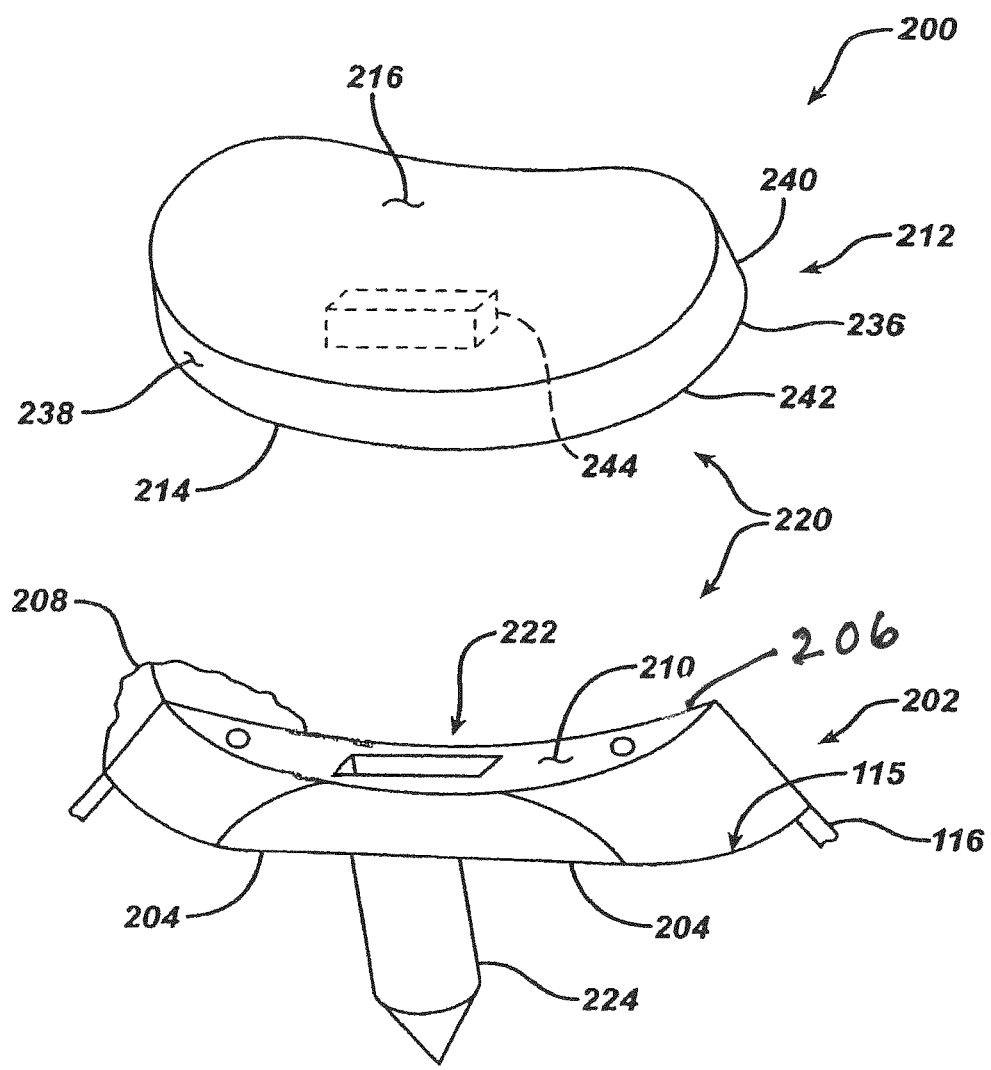
FIG. 13 is an exploded perspective view of the glenoid assembly of FIG. 12.

According to the present invention and referring now to FIGS. 12 and 13, an augmented gleniod implant assembly 200 to shown for use in the glenoid fossa 115 of the scapula 116. The implant assembly 200 includes a first component 202 for attachment to the scapula 116. The first component 202 defines a support surface 204 for cooperation with the glenoid fossa 115. The first component 202 also includes a second surface 206 adapted to be adjacent, a buttress 208 formed in the glenoid fossa 115 of the scapula 116. The first component 202 also includes an assembly face 210 opposed to the support surface 204. The implant assembly 200 further includes a second component 212. The second component 212 is removably secured to the first component 202. The second component 212 includes an assembly phase 214 of the second component 212. The assembly 214 of the second component 212 is in close approximation to the assembly surface 210 of the first component 202. The second component 212 further includes an articulating surface 216 opposed to the assembly surface 214.

The augmented glenoid implant assembly 200 including the first component 202 and the second component 212 may be made of any suitable, durable material. For example, the first component 202 and or the second component 212 can be made of a metal. For example, if made of a metal the first component 202 and the second component 212 may be made of a cobalt chromium alloy, a titanium alloy, or a stainless steal alloy. The components 202 and 212 may be made of a biologic, a ceramic, an alumna, a zirconia, a carbon fiber material, a composite, or a plastic. If made of a plastic the first component 202 and the second component 212 may be made of, for example, an ultra high molecular weight polyethylene. For example, the second component 212 and the first component 202 can be made of cross-linked high ultra high molecular weight polyethylene, for example a product sold by DePuy Orthopaedics, Inc. as Marathon® and as disclosed in U.S. Pat. No. 6,228,900 to Mckellop et al.

Figure 14:
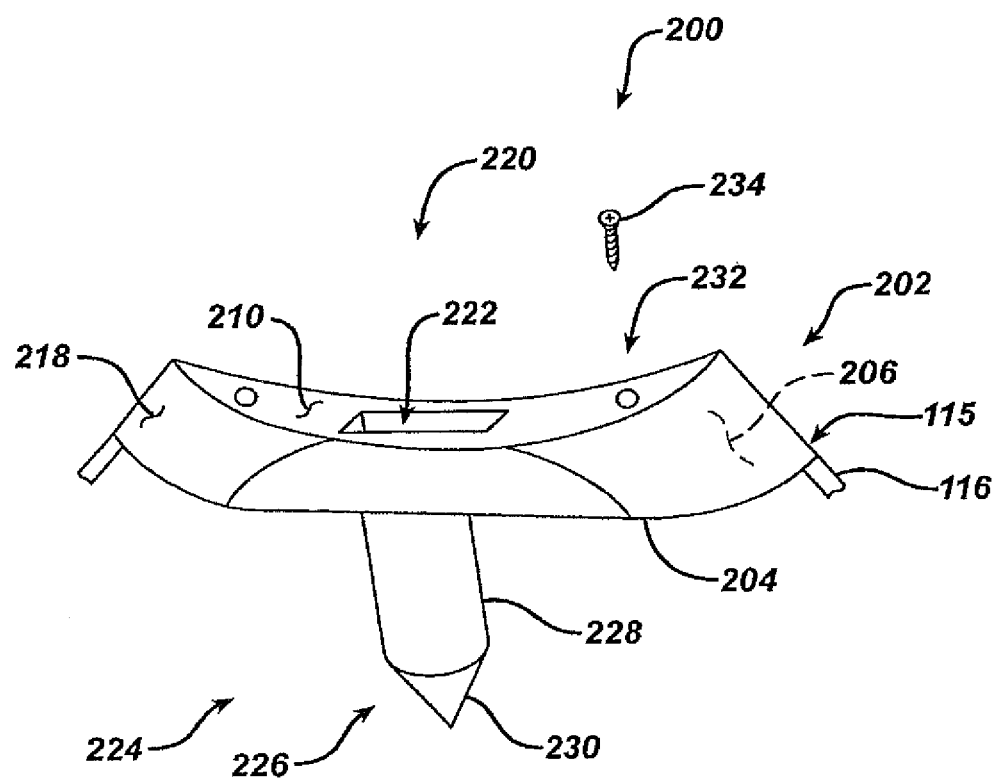
FIG. 14 is a perspective view showing a modular augmented glenoid component of the glenoid assembly of FIG. 12 in accordance with another embodiment of the present invention.

Referring now to FIG. 14, the first component 202 is shown in greater detail. The first component 202 may have any suitable shape capable of providing for a glenoid implant assembly 200 to the patient. The first component 202 may have a shape conforming to the posterior defect of the glenoid. The first component 202 may have a shape corresponding to a cavity prepared with a buttress or step as shown in U.S. Pat. No. 6,699,289.

As shown in FIG. 14, the second component 202 may include assembly surface 210 for assembly with the second component 212 as well as the support surface 204, which is spaced apart from the assembly surface 210. The support surface 204 and the assembly surface 210 may be spaced apart and generally parallel with each other.

The support surface 204 may have any suitable shape and may for simplicity be planar. Alternatively, the support surface 204 may be arcuate. It should be appreciated that the support surface 204 can conform to a surface easily prepared in the scapula by commercially available orthopaedic instrumentation.

The assembly surface 210 may be any suitable surface and may be planar or accurate. The assembly surface 210 should be designed to be combatable with the mating surface of the second component 212. The second surface 206 of the first component 202 is adapted for close proximity to the buttress prepared in the glenoid cavity. For example and for simplicity, the second surface 206 may be planar to conform to a buttress machined into a glenoid fossa 115 of the scapula 116.

As shown in FIG. 14, the first component 202 includes a periphery 218, which may have any suitable shape. The periphery 218 may have, for example, a shape similar to the shape of the natural glenoid fossa.

As shown in FIG. 14, the glenoid implant assembly 200 may include a locking or securing feature 220 to secure the second component 212 to the first component 202. The locking feature 220 may include a first component locking feature 222. The first component locking feature 222 may be in the form of, for example and as is shown in FIG. 14, a cavity or void 222. The void 222 may have any suitable shape and may, for example and as is shown in FIG. 14, have a rectangular cross section. It should be appreciated that the void 222 may have any suitable shape, such as a cylindrical, triangular, or any shape.

The augmented glenoid implant assembly 200 may include a securing feature 224 for assisting and securing the first component 202 to the scapula 116. The securing feature 220 my include a first securing feature 226 that is operably assisted with the first component 202. The first securing feature 226 may, as shown in FIG. 14 extend downwardly from support surface 204 of the first component 202. The first securing feature 226 may have any suitable shape for providing securement to the first component 202 to the scapula 116. The first securing feature 226 may as shown in FIG. 14 have a generally cylindrical shape.

The first securing feature 226 as shown in FIG. 14, may be in the form of a peg 226 including a cylindrical portion 228 extending from the support face 204 of the first component 202 and a conical portion 230 extending from the cylindrical portion 228.

The securing feature 224, as is shown in FIG. 14, may also include a second securing feature in the form of spaced apart openings 232 for cooperation with fasteners 234. The fasteners 234 may be in the form of cortical screws for engagement with cortical bone of scapula.

Figure 15:
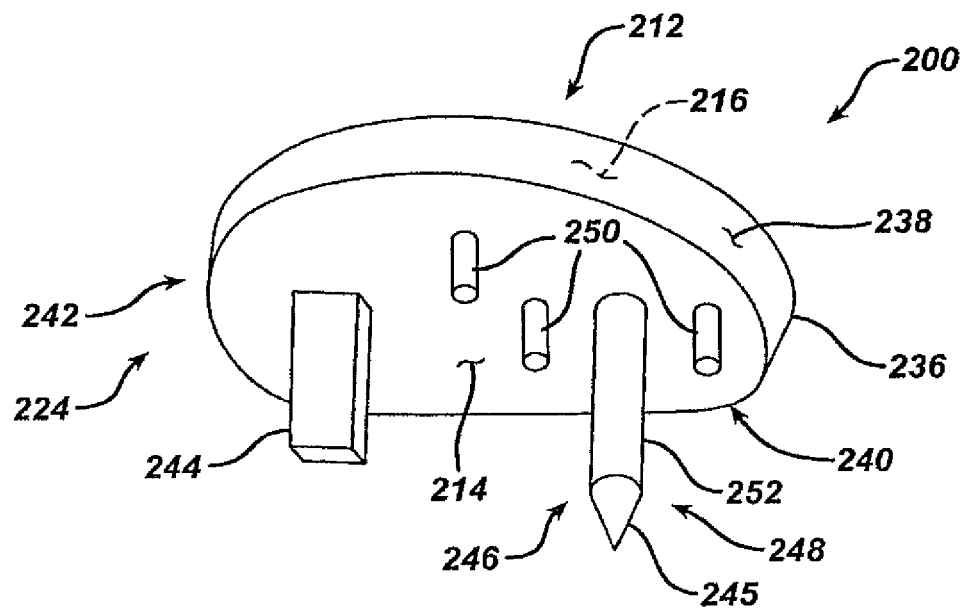
FIG. 15 is a bottom, right-angled perspective view of an embodiment of a glenoid bearing for cooperation with the modular augmented glenoid component of FIG. 14.
Figure 16:
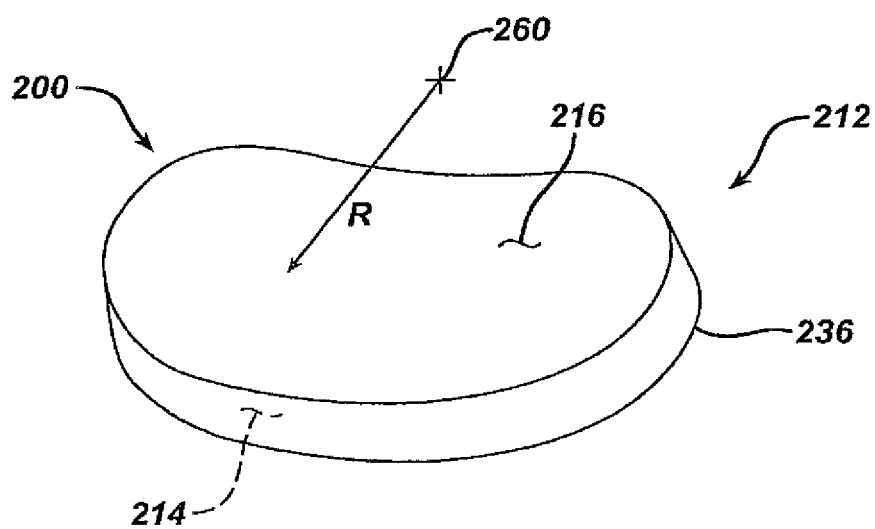
FIG. 16 is a top, left-angled perspective view of the glenoid bearing of FIG. 15.

Referring now to FIGS. 15 and 16, the second component 212 of the augmented glenoid implant assembly 200 is shown in greater detail. The second component 212 may be made of any suitable, durable material. Preferably the material for the second component 212 is sterilizible by a commercially available sterilization technique. Such sterilization techniques include autoclaving, gamma irradiation as well as other processes.

The second component 212 may be made of a metal, a biological material, ceramic, alloy, zirconium, a carbon fiber material, a composite, or a plastic. If made of a metal, the second component 212 may be made of, for example, cobalt chromium alloy, a stainless steel alloy, or a titanium alloy. If made of a plastic, the second component 212 may be made of, for example, polyethylene. The second component can be made of an ultra high molecular weight polyethylene. If made of an ultra high molecular weight polyethylene the second component may be made of a cross-linked material, for example, polyethylene sold by DePuy Orthopaedics, Inc. as Marathon® plastic.

The second component 212 may have any suitable size and may be adapted to conform to the shape of the natural glenoid. The second component 212, as is shown in FIG. 13, may include a body 236. The body 236 defines an articulating surface 216 and an opposed assembly surface 214. The body 236 further includes a periphery 238 between the articulating surface 216 and the assembly surface 214. The second component 212 of the implant assembly 200 may include a mounting portion 240 for cooperation with the impaired glenoid and an assembly portion 242 for cooperation with the assembly surface 210 of the first component 202.

The second component 212 may include a second component locking feature 244 of the second component 212 in the form of, for example and as is shown in FIG. 13, a protrusion. Protrusion 244 is adapted with cooperation with the void 222 of the first component 202. The locking feature 244 and the void 222 form securing feature 224.

The second component 212 may also include a mounting feature 246 for assisting and securing the second component 212 to the glenoid 115 of the scapula 116. For example and as is shown in FIG. 15, the mounting feature 246 may include a center peg 248 extending downwardly from assembly surface 214 of the second component 212. In addition to the center peg 246, additional pegs 250 may likewise extend downwardly from the assembly surface 214 of the second component 212.

The pegs 248 and 250 may have any suitable size and shape and may, as is shown in FIG. 15, be generally cylindrical including a cylindrical portion 252 extending from the mounting portion 240 from the assembly face 214 and including a conical portion 254 extending from the cylindrical portion 252. It should be appreciated that the pegs 248 and 250 may have any alternative shape, for example, a triangular or rectangular shape. The pegs 248 and 250 may alternatively have a tapered or other non-uniform cross section.

Figure 15A:
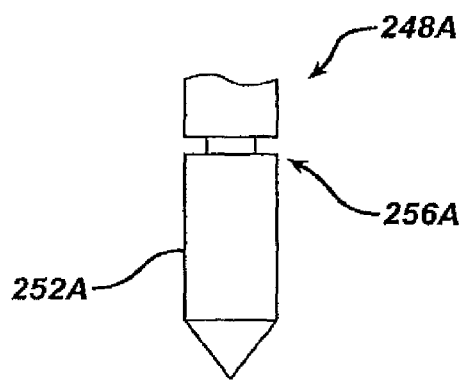
FIG. 15A is a partial plane view of a glenoid bearing with a grooved anchor peg.

Referring now to FIG. 15A, an alternative embodiment of the pegs 248 and 250 is shown as peg 248A including recess 256A formed in cylindrical portion 252A of the peg 248A. It should be appreciated that the peg 248A may be suitable for the pegs of the second component 220 as well as for peg 226 of the first component 202.

Figure 15B:
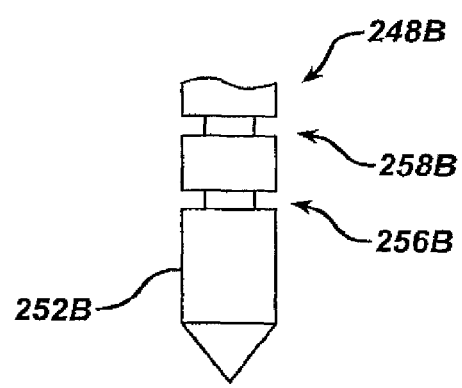
FIG. 15B is a partial plane view of a glenoid bearing with a double grooved peg.

Yet another form of a peg for use with the first and second components of the augmented glenoid assembly of the present invention is shown as peg 248B in FIG. 15B. The peg 248B is similar to the peg 248A of the FIG. 15A, except that the peg 248B includes a second angular groove 258B spaced from a first angular groove 256B. The grooves 256B and 258B are formed in cylindrical portion 252B of the peg 248B.

Figure 15C:
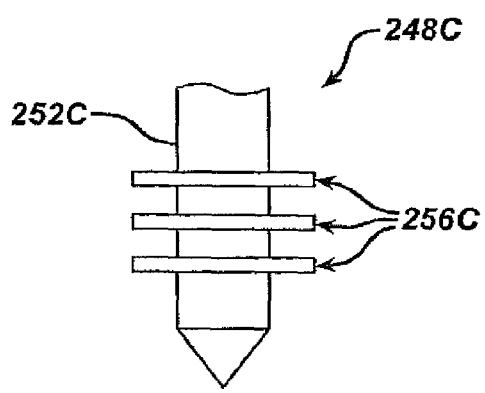
FIG. 15C is a partial plane view of a glenoid bearing with a flexible finned.

Referring now to FIG. 15C, yet another embodiment a peg for use in a component of the modular glenoid implant assembly of the present invention is shown as peg 248C. The peg 248C includes a plurality of pliable fins 256C formed on cylindrical portion 252C of the peg 248C. The pliable fins 256C are designed to bend or deflect on insertion to prevent the removal of the pegs 248C.

Figure 15D:
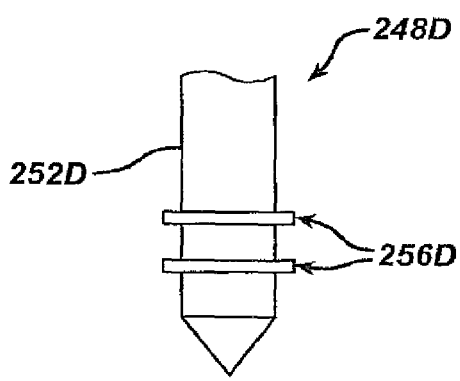
FIG. 15D is a partial plane view of a glenoid bearing with a finned peg.

Referring now to FIG. 15D, yet another form of a peg for use in the glenoid implant assembly of the present invention is shown as peg 248D. The peg 248D includes a series of rings 256D, that extend past the cylindrical portion 252D of the peg 248D. The rings 256D serve to assist in locking the pegs 248D into the glenoid cavity of the scapula 116.

Referring now to FIG. 16, the articulating surface 216 of the second component 212 of the glenoid assembly 200 is shown in greater detail. The articulating surface 216 is opposed to the assembly surface 214 of the body 236 of the second component 212. The articulating surface 216 is as shown in FIG. 14, preferably replicates the glenoid fossa. Therefore, the articulating surface 216 is preferably concave. For example, the articulating surface 214 may be defined by a radius R extending from origin 260.

Referring now to FIG. 17, the augmented glenoid assembly 200 is shown in position on the scapula 116. First component 202, as is shown in FIG. 17, may be positioned on the eroded posterior portion 262 of the scapula 116. The peg 226 of the first component 202 is secured into the scapula 216. The support surface 204 of the first component 202 and the second surface 206 of the first component 202 are positioned against the repaired resected surfaces of the glenoid fossa 115. The second component 212 may be positioned against the assembly surface 210 of the first component 202. The assembly surface 214 of the second component 212 may be positioned against the assembly surface 210 of the first component 202.

As shown in FIG. 17, the second component 212 may extend beyond the first component 202, and may as is shown in FIG. 15, extend to an anterior portion 264 of the scapula 116. The mounting portion 240 of the assembly surface 214 of the second component 212 may rest against a prepared surface of the glenoid fossa 115 of the scapula 116. The first component 202 may be secured to the second component 212 by means of the locking feature 220. The protrusion 244 is inserted into the void 222 of the first component 202. The second component 212 may further include mounting or securing feature 246 in the form of the central peg 248 and the mounting pegs 250. The pegs 248 and 250 are inserted into cavities 266 formed in the scapula for receiving the pegs 248 and 250. The cavities 266 may be generally cylindrical for receiving the pegs 248 and 250.

Figure 18:
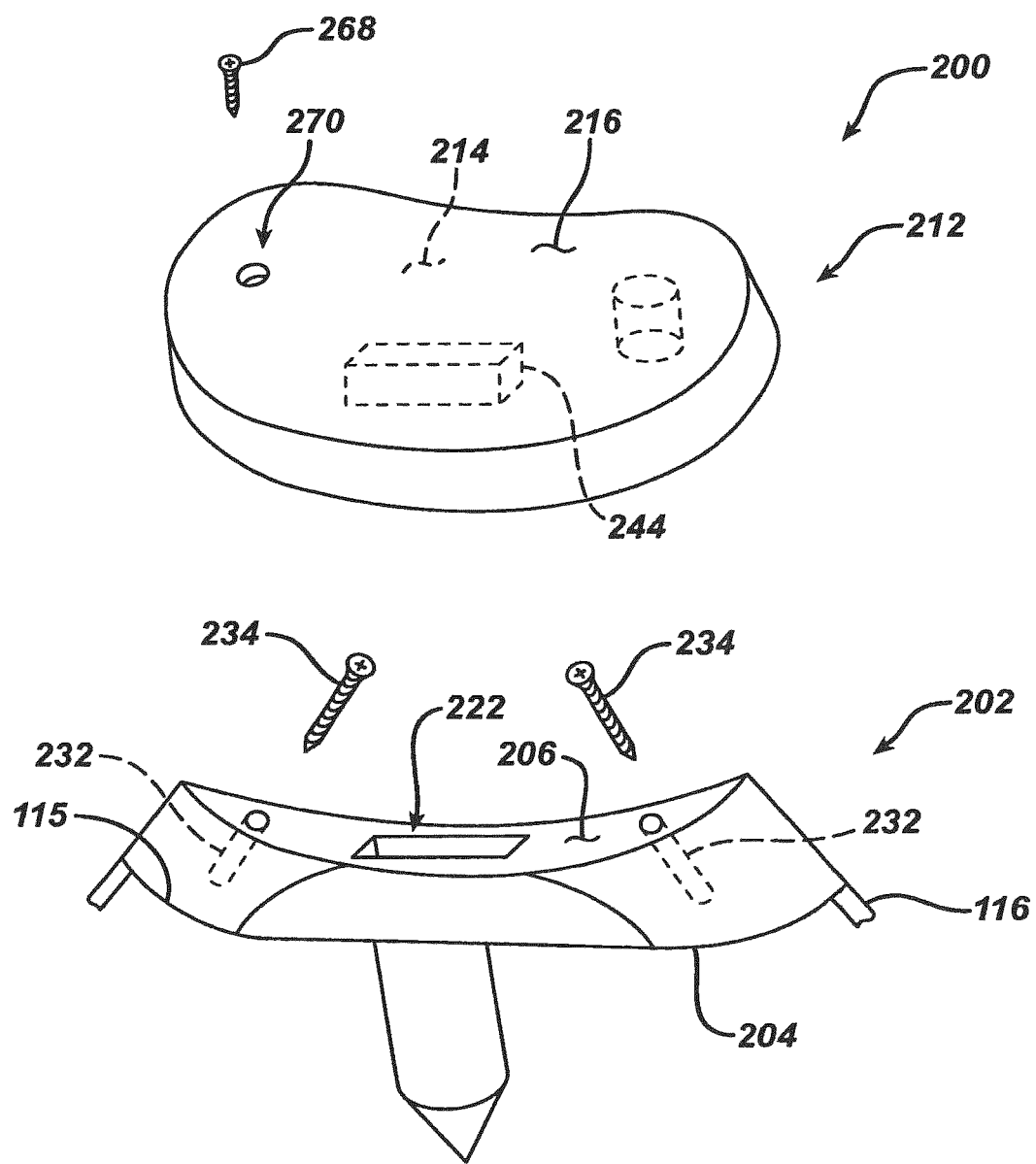
FIG. 18 is an exploded perspective view of the glenoid assembly of FIG. 12 including fastener.

Referring now to FIG. 18, the first component 202 may be secured to the scapula 116 by means of fasteners. For example and is shown in FIG. 18, first component 202 may include two spaced apart openings 232 for receiving fasteners 234 in the form of, for example, cancellous screws. The first component 202 is positioned on the scapula 116 and the screws 234 are positioned through openings 232 and are tightened against the scapula 116 to secure the first component 202 to the scapula 116. After the screws 234 are fully seated, the second component 212 is positioned on the first component 202.

It is desirable to provide the articulating surface 216 of the glenoid implant assembly 200 with a smooth surface for articulation with the humeral component of a prosthesis. However, the implant assembly may be provided with a securement of the second component 212 that may include fasteners 268, which cooperate with openings 270 formed through the articulating surface 216 of the second component 212. The fasteners 268 may be in the form of a cancellous screws, which mate with the cancellous bone and the scapula 116 to assist in securing the second component 212 to the scapula 116.

Referring again to FIG. 13, the locking feature 220 may be any feature to assist in securing the second component 212 to the first component 202. For example, and is shown in FIG. 13, the second component 212 includes protrusion 244 while the first component 202 includes void 222, which is adapted for cooperation with the protrusion 244. It should be appreciated that the void 222 may be positioned in the second component 212 and the protrusion 244 may be positioned in the first component 202.

The protrusion 244 may have any shape and may as is shown in FIG. 13 be generally rectangular in cross section. The void 222 may likewise have a shape that preferably can conform to the protrusion 244. As shown in FIG. 13, the void 222 is in the form of a rectangular slot having a uniform cross-section to match that of the protrusion 244.

Figure 18A:
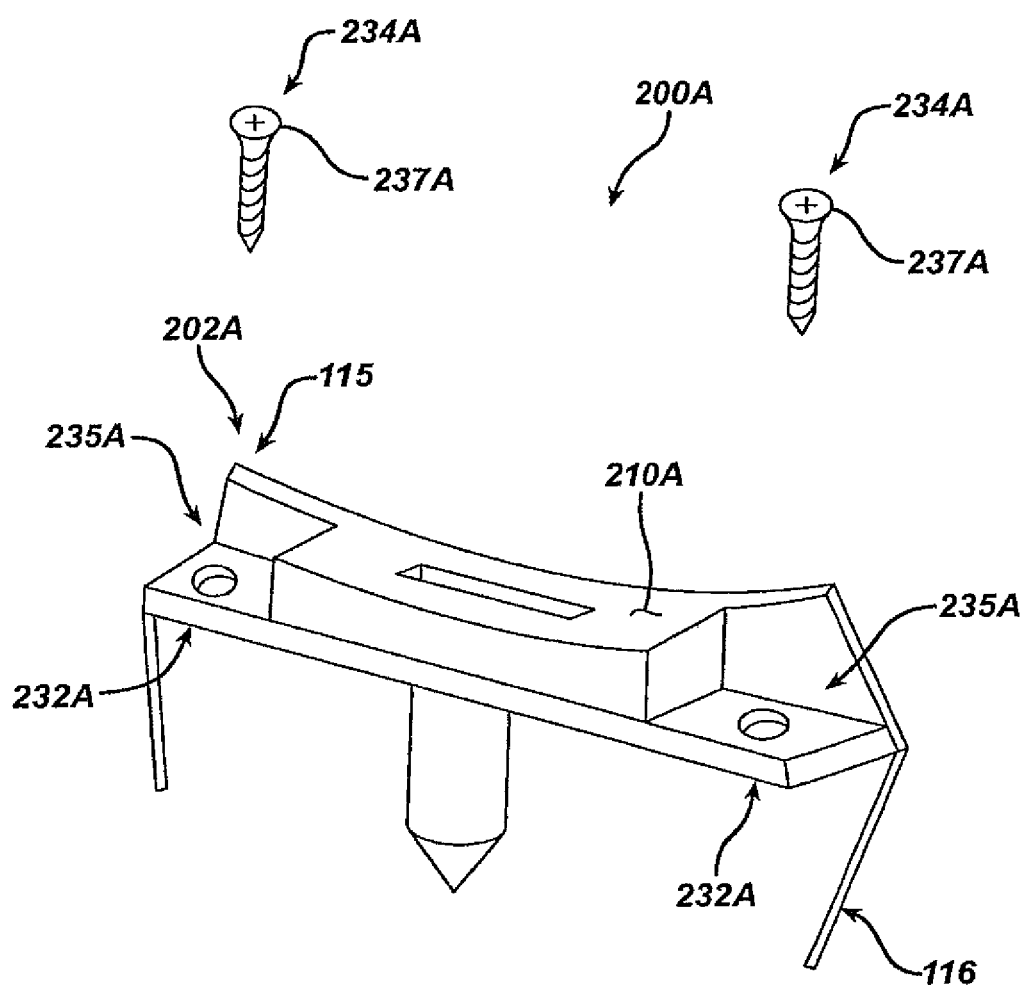
FIG. 18A is a perspective view showing a modular augmented glenoid component in accordance with another embodiment of the present invention showing alternate provisions for fasteners to secure the component

Referring now to FIG. 18A, another embodiment of the present invention is shown as augmented glenoid implant assembly 200A. The glenoid implant assembly 200A is similar to the glenoid implant assembly 200 of FIGS. 12-18 except that the first component 202A of the glenoid implant assembly 200A is slightly different than the first component 202 of the glenoid implant assembly 200 of FIGS. 12-18. The first component 202A of the first embodiment 200A includes a pair of spaced apart pockets 235A positioned over openings 232A of the first component 202A. The openings 232A are sized for passage of the screws 234A through the openings 202A. The pockets 235A are used to provide for the location heads 237A of the screws 234A.

Figure 18B:
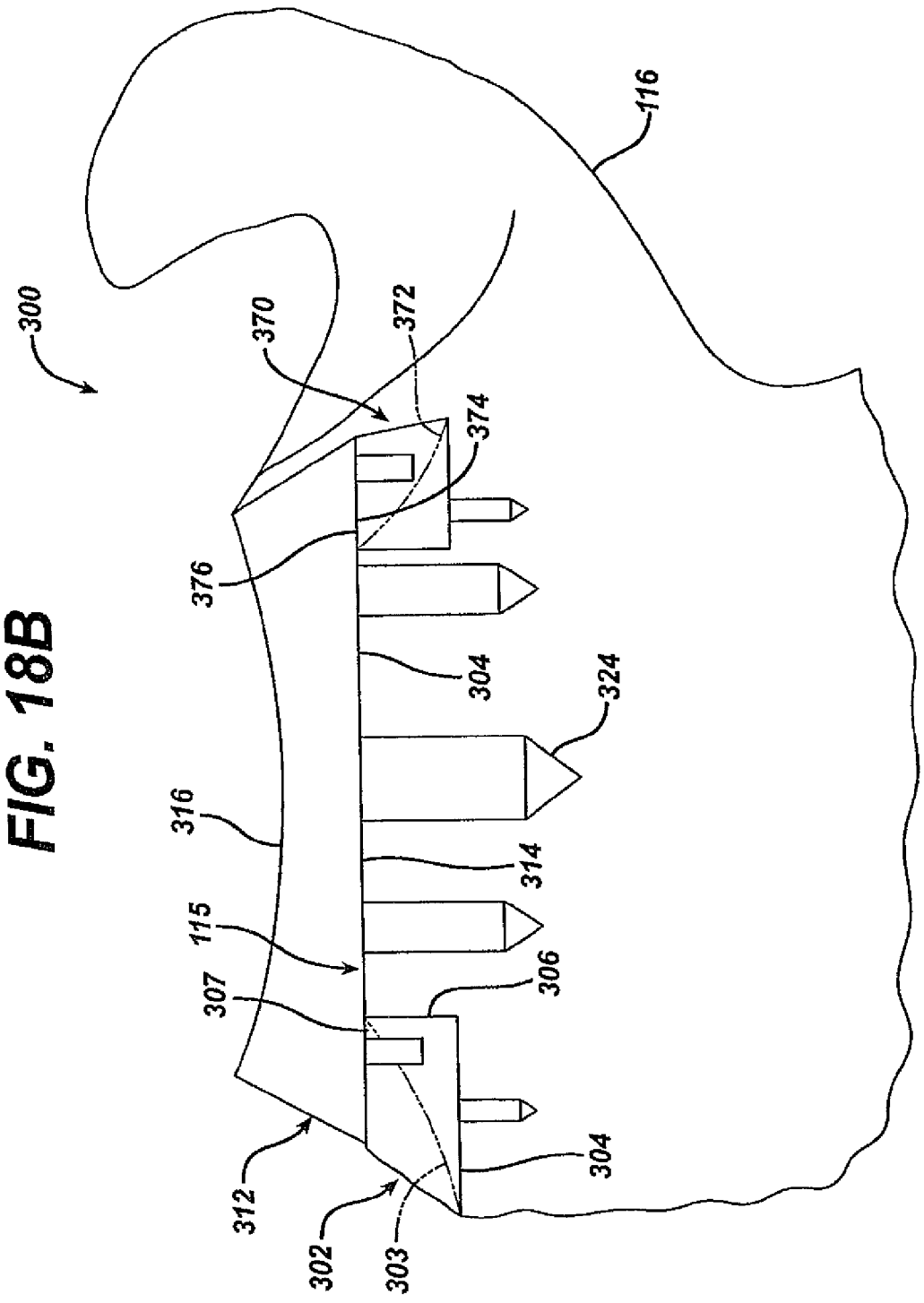
FIG. 18B is an plan view partially in cross section showing a modular augmented glenoid component in accordance with another embodiment of the present invention having a two piece reinforced second component in position on a glenoid.

Referring now to FIG. 18B, another embodiment of the present invention is shown as glenoid implant assembly 300. The glenoid implant assembly 300 is similar to the glenoid implant assembly 200 of FIGS. 12-19 except that the glenoid implant 300 is for use where, in addition to a posterior defect a second defect exists. For example, an anterior defect may also exist in the glenoid fossa 115 of the scapula 116.

For example, and as is shown in FIG. 18B, the glenoid implant assembly 300 includes a first component 302. The first component 302 is used to accommodate a posterior defect 303 as shown in phantom. The first component 302 is for attachment to the scapula 116. The first component 302 defines the support surface 304 for cooperation with the glenoid fossa 115 and a second surface 306 positioned adjacent a buttress 307 formed in the glenoid fossa 115. The first component 302 includes an assembly face 310.

The augmented glenoid assembly further includes a second component 312. The second component is removably secured to the first component 302. The second component 312 includes an assembly surface 314. The assembly surface 314 of the second component 312 is in close approximation with the first component 302. The second component 312 further includes an articulating surface 316 opposed to the assembly surface 314.

The glenoid assembly 300 further includes a third component 370. The third component 370 is utilized to accommodate an anterior defect 372. The third component 370 defines a support surface 374 for cooperation with the glenoid fossa 115. The third component 370 further includes an assembly face 376. The third component 370 is in the juxtaposition with the second component 312. The assembly surface 314 of the second component 312 is in close approximation to the assembly surface 376 of the third component 370.

Referring now to FIG. 18C-18F, another embodiment of the present invention is shown as glenoid implant assembly 400. The glenoid implant assembly 400 of FIGS. 18C-18F is similar to the glenoid implant 200 of FIGS. 12-18 except the glenoid implant assembly 400 includes a second component 312 that is an assembly of two separate components.

Figure 18C:
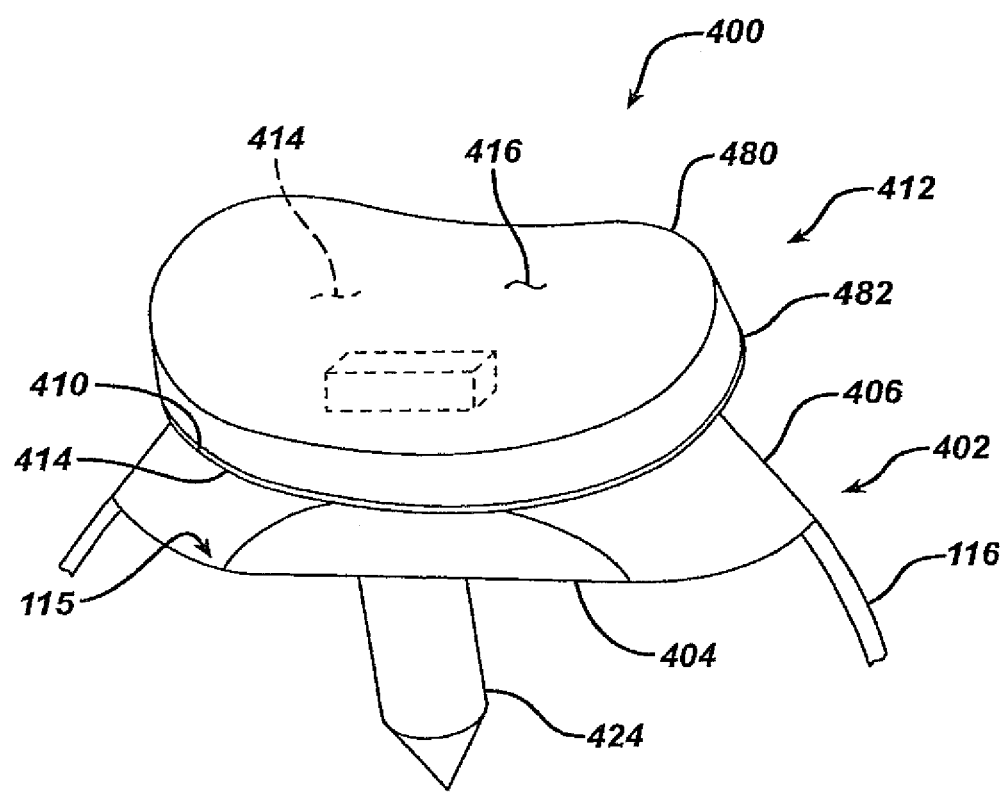
FIG. 18C is a perspective view of the modular augmented glenoid assembly of FIG. 18B.
Figure 18E:
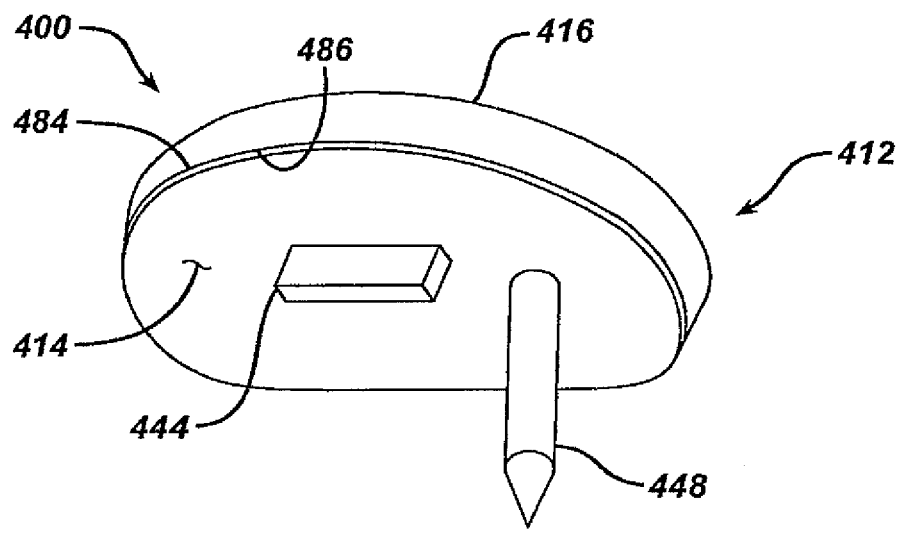
FIG. 18E is a perspective view of the second component of the modular augmented glenoid assembly of FIG. 18B.
Figure 18F:
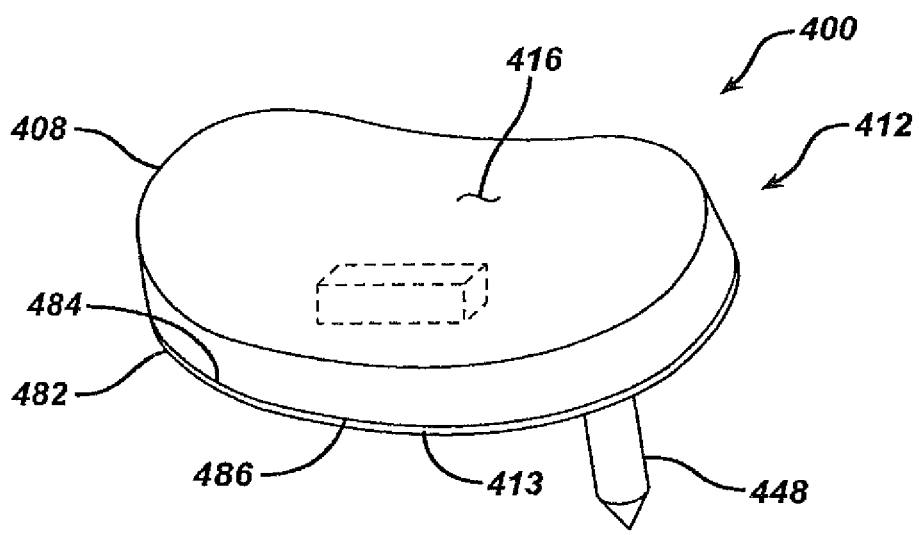
FIG. 18F is another perspective view of the second component of the modular augmented glenoid assembly of FIG. 18B.

Referring now to FIG. 18C, the glenoid implant assembly 400 includes a first component 402 and a second component 412. The first component 402 is similar to the first component 202 of the glenoid implant assembly 200 of FIGS. 12-18. The first component 402 includes a support surface 404 for cooperation with the scapula 116 as well as a second surface 406 for cooperation with a buttress formed on the scapula 116. The second component 406 further includes an assembly surface 410 for contact with the second component 412. The first component 402 may further include a securing feature 424 in the form of, for example, a peg.

Glenoid implant assembly 400 also includes the second component 412. The second component 412 is somewhat similar in size and shape to the second component 212 of the augmented glenoid implant assembly 200 of FIGS. 12-18 except that the second component 412 is made from two components including a bearing component 480 and a backing component 482. The backing component 482 defines the assembly surface 414 for cooperation with assembly surface 410 of the first component 402. The bearing component 480 defines an articulating surface 416.

Referring now to FIG. 18D, the augmented glenoid implant assembly 400 is shown in an exploded view. The augmented glenoid implant assembly 400 as shown in FIG. 18D may include a locking feature 420 for locking the second component 412 to the first component 402. For example and is shown in FIG. 18D, the backing component 482 of the second component 412 may include a protrusion 444 for cooperation with a void 422 formed in first component 402.

The augmented glenoid implant assembly 400 of FIGS. 18C-18F, may include securing features to assist in securing the glenoid assembly 400 to the scapula 116. For example and is shown in FIG. 18D, the first component 402 may include a securing feature 424 in the form of a peg. The second component 412 may include a securing feature 448 in the form of, for example, a peg.

The first component 402 and the second component 412 may be made of any suitable, durable material. Preferably the materials for which the first component 402 and the second component 412 are sterilizable. Component 402 may be made of, for example, a metal, a plastic, a ceramic, or a composite material.

The second component 412 includes the backing component 482 and the bearing component 480. The backing component 482 may be made of any suitable, durable material. For example, the backing component 482 may be made of a plastic or a metal, a composite, or a ceramic. For simplicity and to provide a mechanical or structural support for the bearing component 480, the backing component 480 may be made of a metal. If made of a metal the backing component 482 may be made of, for example, cobalt chromium alloy, a titanium alloy, or a stainless alloy.

The bearing component 480 may be made of any suitable, durable material. For example, the bearing component 482 may be made of a ceramic, a composite, a plastic, or a metal. If made of a plastic, the bearing component 480 may be made of an ultra-high molecular weight polyethylene. If made of an ultra-high molecular weight polyethylene the bearing 480 may be made of a cross-linked, ultra-high molecular weight polyethylene such as Marathon®.

The backing component 482 includes a second component assembly surface 484, which mates with a second component assembly surface 486 of the bearing component 480. The bearing component 480 is preferably securely fastened to the backing component 482.

The bearing component 480 may be secured to the backing component 482 in any suitable fashion. For example, the bearing component 480 may be, glued, welded, molded, or interferingly fitted to the backing component 482. For example and is shown in FIG. 18D, the bearing component 480 may be secured to the backing component 482 by molding the bearing component 480 unto the backing component 482.

To assure the successful adherence of the bearing component 480 to the backing component 482, the backing component 482 may include a porous surface on assembly surface 484. The porous surface may be, for example, Porocoat® provided by DePuy Orthopaedics, Inc. and generally described in U.S. Pat. No. 3,855,638 to Pilliar et al.

Figures 19, 20:
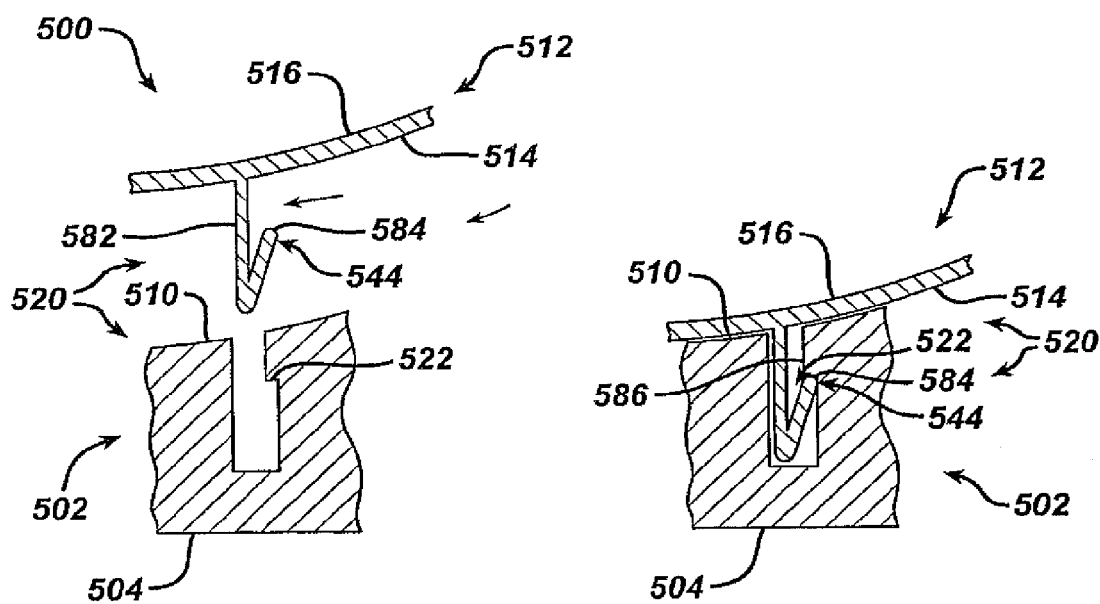
FIG. 19 is an exploded partial plan view of yet another embodiment of the present invention in the form of a modular augmented glenoid assembly including a locking feature in the form of a tab and a cavity.
FIG. 20 is a partial plan view of the modular augmented glenoid assembly of FIG. 19.

Referring now to FIGS. 19 and 20, another embodiment of the present invention is shown as augmented glenoid assembly 500. The augmented glenoid assembly 500 of FIGS. 19 and 20 is generally similar to the glenoid assembly 200 of FIGS. 12-18. The glenoid implant assembly 500 includes a second component 512, which is lockably engaged to the first component 502. The first component 502 includes a support surface 504 for contact with the scapula 116. The first component 502 further includes an assembly surface 510. The second component 512 includes an articulating surface 516 and an opposed assembly surface 514.

A locking feature 520 secures the second component 512 to the first component 502. The locking feature 520 includes a first component locking feature 522 in the form of a cavity, which designed to receive second component locking feature 544 in the form of a protrusion. The protrusion 544, as is shown in FIGS. 19 and 20, includes a stem 584 extending from the assembly surface 514 of the second component 512. The protrusion 544 further includes a pliable tab 584 extending from the stem 582. The first component locking feature or cavity 522 includes an internal lip 586 for constraining the tab 584 when the second component 512 is engaged in the first component 502 (see FIG. 20).

Figure 21A:
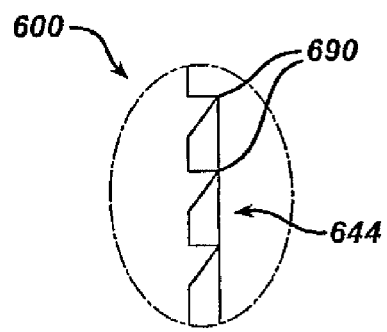
FIG. 21A is a partial view of the protrusion of the second component of the glenoid assembly of FIG. 21 showing the teeth of the protrusion.
Figure 21:
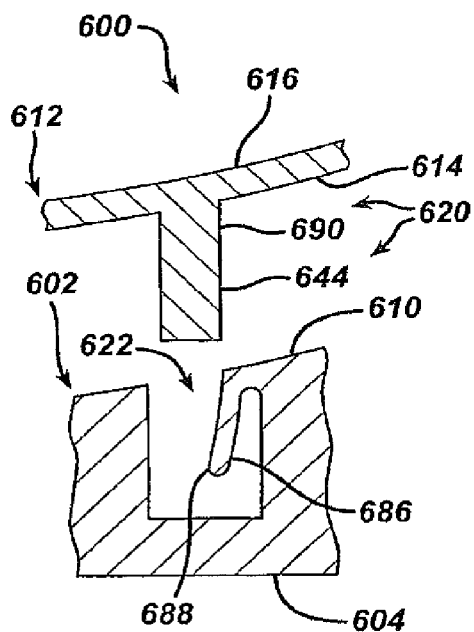
FIG. 21 is an exploded partial plan view of another embodiment of the present invention in the form of a modular augmented glenoid assembly including a locking feature in the form of a protrusion and a void with an urging member.
Figure 22:
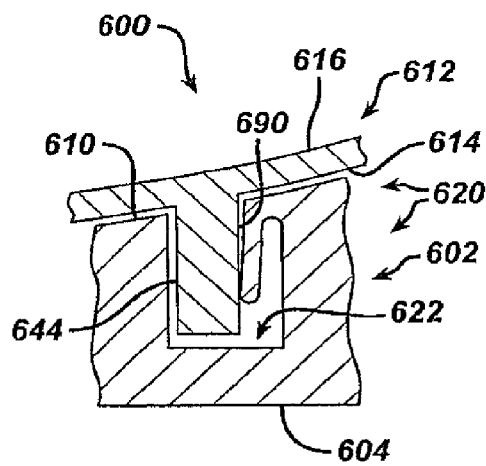
FIG. 22 is a partial plan view of the modular augmented glenoid assembly of FIG. 21.

Referring now to FIGS. 21 and 22, yet another embodiment of the present invention is shown as augmented glenoid implanted assembly 600. The augmented glenoid implant assembly 600 is generally similar to the glenoid assembly 200 of FIGS. 12-18, but includes a locking feature 620 that is somewhat different than the locking feature 220 of the glenoid implant assembly 200 of FIGS. 12-18.

The glenoid implant assembly 600 includes a first component 602 having a support surface 604 and an opposed surface 610. A void or cavity 622 is formed from the assembly surface 610 of the first component 602. An urging member 686 extends into the cavity 622 of the first component 602. The urging member 686 is preferably resilient and includes an edge 688, which protrudes outwardly from the urging member 686.

The glenoid implant assembly further includes the second component 612 having an articulating surface 616 and an opposed assembly surface 614. A protrusion 644 extends outwardly from assembly surface 614.

Referring now to FIG. 16-21A, the protrusion 644 includes a plurality of teeth 690 extending from the protrusion 644. The teeth 690 are adapted for engagement with the edge 688 of the urging member 686 when the second component 612 is in position with first component 602 (see FIG. 22).

Figure 23A:
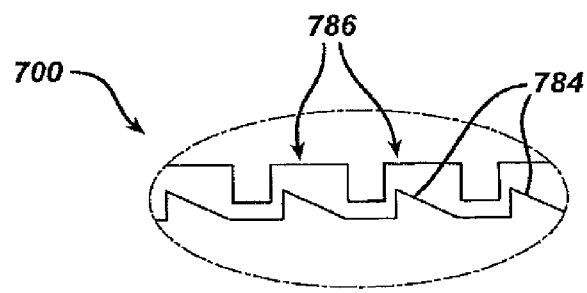
FIG. 23A is an enlarged view of the pin and an opening of FIG. 23.
Figure 23:
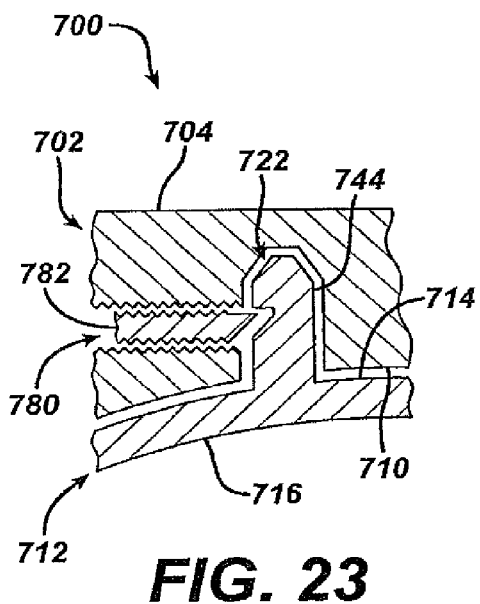
FIG. 23 is an exploded partial plan view of a further embodiment of the present invention in the form of a modular augmented glenoid assembly including a locking feature in the form of a pawl and a notch.
Figure 24:
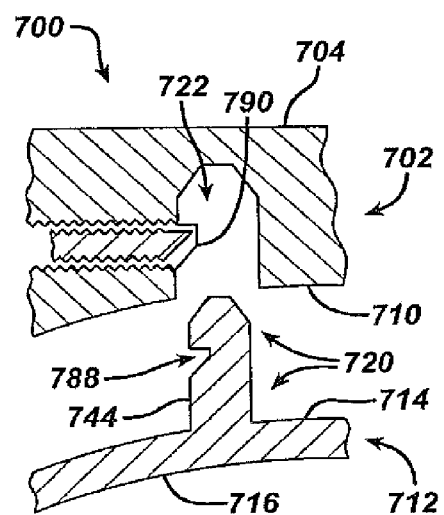
FIG. 24 is a partial plan view of the modular augmented glenoid assembly of FIG. 23.

Referring now to FIGS. 23 and 24, yet another embodiment of the present invention is shown as glenoid implant assembly 700. The glenoid implant assembly 700 is similar to the glenoid implant assembly 200 of FIGS. 12-18 except that the glenoid implant assembly 700 includes a locking feature 720 that is somewhat different than the locking feature 220 of the glenoid implant assembly 200 of FIGS. 12-18.

The glenoid implant assembly 700 includes a first component 702 having a support surface 704 and an opposed surface 710. A locking feature in the form of a void 722 extends inwardly from the assembly face 710. The first component 702 may further define an opening 780 for receiving a pin 782. While the pin 782 may be interferencely fitted to the opening 780, the pin 782 may include a plurality of teeth 784, which mates with groove 786 formed on the periphery on the opening 780 (see FIG. 23A). The second component may 712 further include a protrusion 744 extending outwardly from the assembly surface 714 of the second component 712. The protrusion 744 may include a notch 788 for cooperation with distal end 790 of the pin 782. The end 790 of the pin 782 matingly engages with the notch 788 of the protrusion 744 to secure the second component 712 onto the first component 702.

According to the present invention and referring now to FIGS. 25 and 26, another embodiment of the present invention is shown as augmented glenoid implant assembly 800. The augmented glenoid implant assembly 800 is similar to the augmented glenoid implant assembly 200 of FIGS. 12-18, but includes a locking mechanism 820, which is different than the locking mechanism 220 of the augmented glenoid implant assembly 200 of FIGS. 12-18.

The glenoid implant assembly 800 includes a first component 802 having a support surface 804 and an opposed assembly surface 810. A cavity 822 extends from support surface 810. The cavity 822 has a pliable wall 880 including a beak 882, which extends inwardly into the cavity 822. The pliable wall 880 includes a wall extension 884 for releasing of the second component 812 from the first component 802.

The augmented glenoid implant assembly 800 further includes second component 812 having an articulating surface 816 and an assembly surface 814. A protrusion 844 extends from the assembly surface 814 of the second component 812. The protrusion 844 includes a lip 890 for cooperation with the beak 882 of the wall 880. When the second component 812 is assembled into the first component 802, the protrusion 844 is positioned in cavity 822. The lip 890 of the protrusion 844 deflects the beak 882 of the wall 880, permitting the protrusion 844 to fully locate in the cavity 822. The beak 882 of the wall 880 locks against the lip 890 of the protrusion 884 securing the second component 812 against the first component 802.

Figure 27:
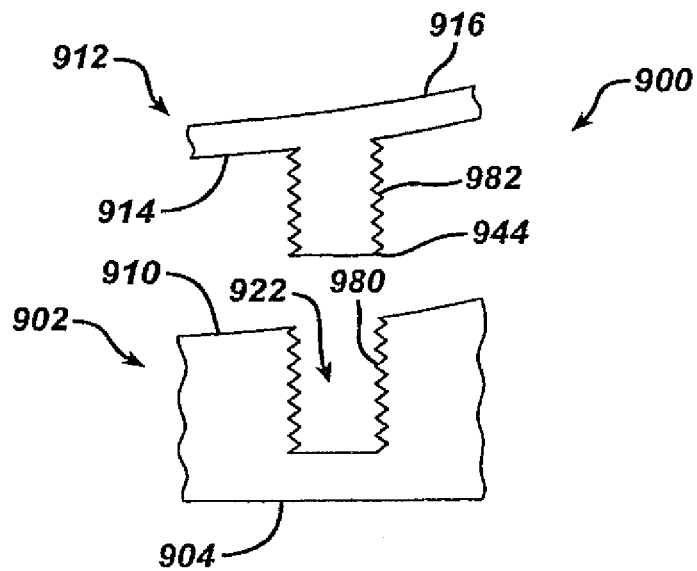
FIG. 27 is an exploded partial plan view of a yet another embodiment of the present invention in the form of a modular augmented glenoid assembly including a locking feature in the form of threads.

Referring now to FIG. 27, yet another embodiment of the present invention is shown as augmented glenoid implant assembly 900. The augmented glenoid implant assembly 900 is similar to the glenoid implant assembly 200 of FIGS. 12-18 and includes a locking mechanism 920, that is different than the locking mechanism 220 of the augmented glenoid implant assembly 200 of FIGS. 12-18.

For example and is shown in FIG. 27, the glenoid implant assembly 900 includes a first member 902 having a support surface 904 and an opposed assembly surface 910. An opening 922 is formed in the assembly 910. The opening 922 includes internal threads 980.

The augmented glenoid implant assembly 900 further includes a second member 912 defining an articulating surface 916 and an opposed assembly surface 914. A protrusion 944 extends from the assembly 914 and is designed to fit in the opening 922. The protrusion 944 includes external threads 982, which mate with internal threads 980 of the opening 922 of the first member 902.

Figure 28:
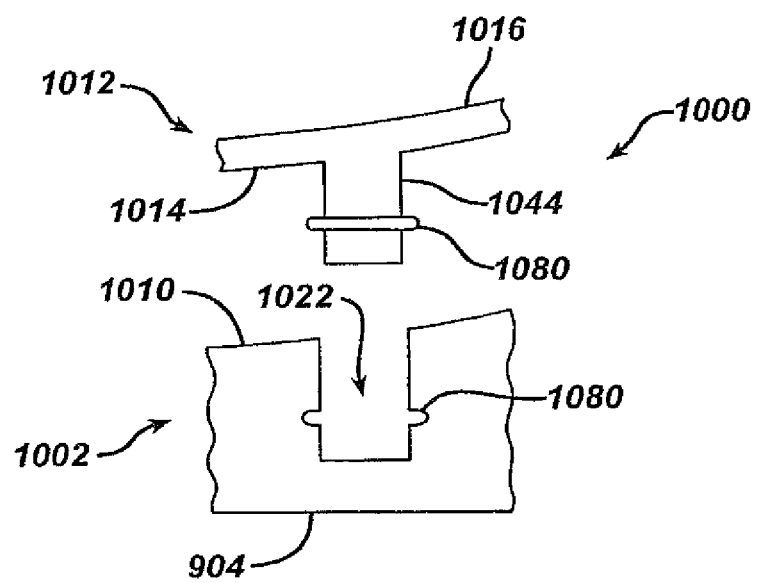
FIG. 28 is an exploded partial plan view of a further embodiment of the present invention in the form of a modular augmented glenoid assembly including a locking feature in the form of a rib.

According to the present invention and referring now to FIG. 28, yet another embodiment of the present invention as an augmented glenoid implant assembly 1000. The augmented glenoid implant assembly 1000 is similar to the augmented glenoid implant assembly 200 of FIGS. 12-18 except that the glenoid implant assembly 1000 includes a locking mechanism 1020, that is different than the locking mechanism 220 of the glenoid implant assembly 200 of FIGS. 12-18.

For example and is shown in FIG. 28, the glenoid implant assembly 1000 includes a first member 1002 having a support surface 1004 and an opposed assembly surface 1010. A void 1022 extends inwardly from the assembly surface 1010.

The glenoid implant assembly 1000 further includes a second member 1012 having an articulating member 1016 and an opposed 1014. A protrusion 1044 extends outwardly from the assembly surface 1014. The protrusion 1022 includes an angular rib 1080, which mates with an angular groove 1082 formed on the first member 1002 in the opening 1022. When the second member 1012 is engaged with the first member 1002 the resilient rib 1080 protrusion 1044 fits in the angular groove 1080 of the opening 1022 to secure the second member 1012 to the first member 1002.

Referring now to FIGS. 29-35, yet another embodiment of the present invention is shown as augmented glenoid implant assembly 1100. The augmented glenoid implant assembly 1100 is similar to the augmented glenoid implant assembly 200 of FIGS. 12-18, but includes a locking feature 1120 which is somewhat different the locking feature 220 of the augmented glenoid implant assembly 200 of FIGS. 12-18.

Figure 29:
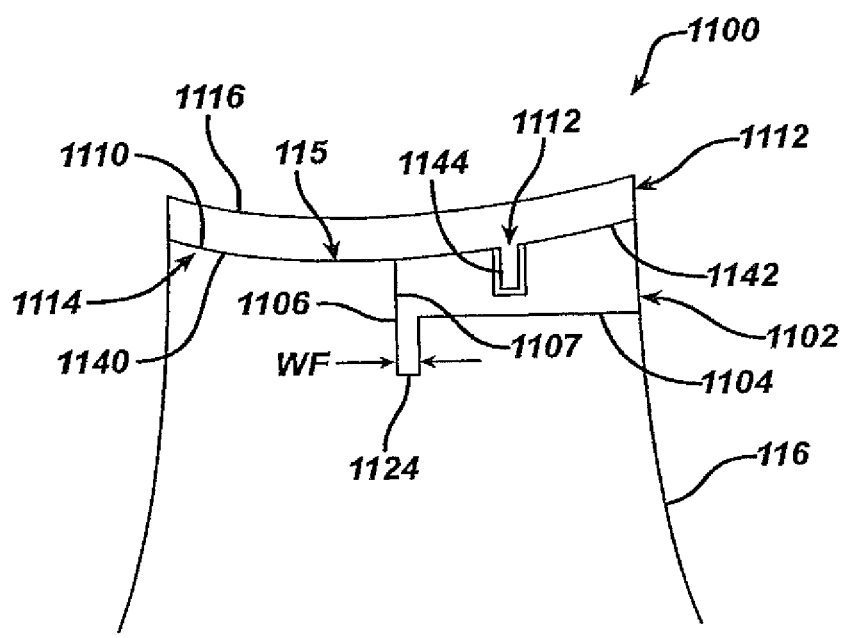
FIG. 29 is an plan view partially in cross section of another embodiment of the present invention in the form of a modular augmented glenoid assembly in position on a glenoid with the locking feature in the form of fin.

For example and is shown in FIG. 29, the augmented glenoid implant assembly 1100 includes a first component 1102 defining a support surface 1104 and an opposed assembly 1110. The first component 1102 further includes a second surface 1106 positioned against buttress 1107 formed in the glenoid fossa 115 of the scapula 116.

The augmented glenoid implant assembly 1100 further includes a second component 1112 defining an articulating surface 1116 and an opposed assembly surface 1114. The assembly surface 1114 includes a mounting portion 1114 for engagement with the glenoid fossa 115 as well as an assembly portion 1142 for engagement with the assembly surface 1110 of the first component 1102.

Figure 30:
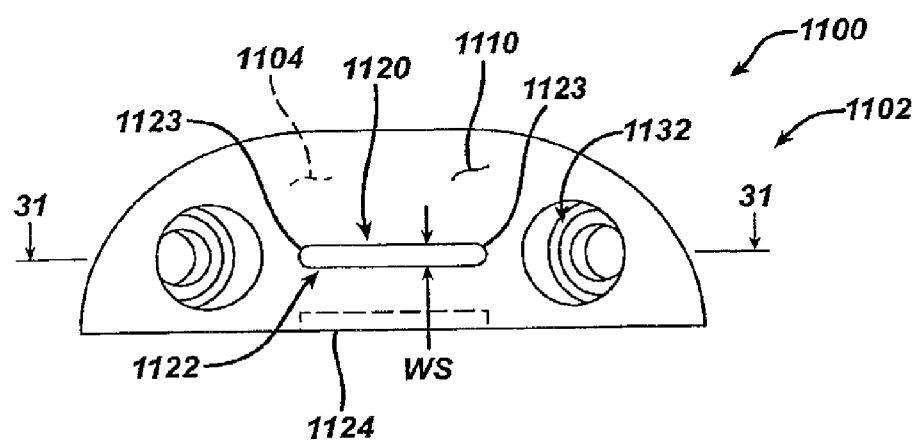
FIG. 30 is a top view of the modular augment glenoid component of the modular augmented glenoid assembly of FIG. 29.
Figure 31:
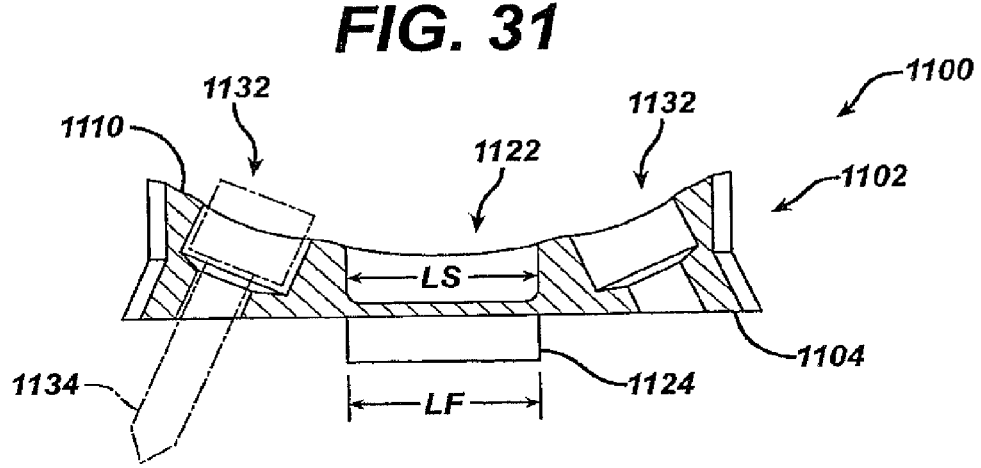
FIG. 31 is a cross section view of the modular augment glenoid component of FIG. 30 along the lines 31-31 in the direction of the arrows.
Figure 32:
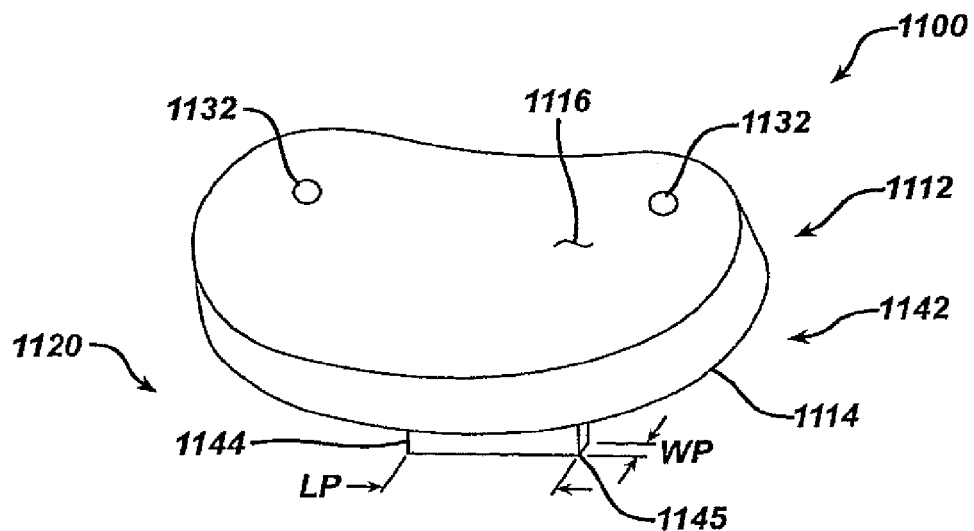
FIG. 32 is a perspective view of the bearing component of the glenoid assembly of FIG. 29.
Figure 32A:
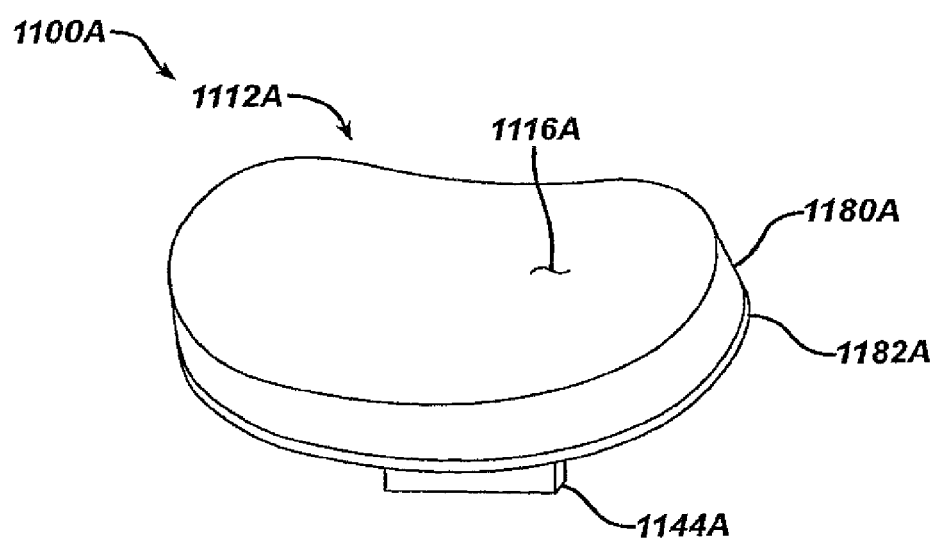
FIG. 32A is a perspective view of an alternate bearing component for use with the modular glenoid component of FIG. 30.
Figure 33:
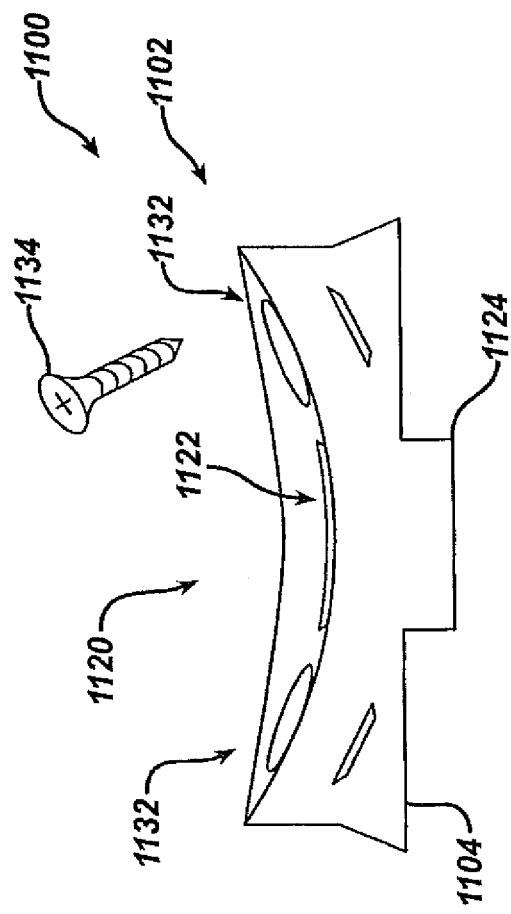
FIG. 33 is a plan view of the modular augment glenoid component of FIG. 30.
Figure 34:
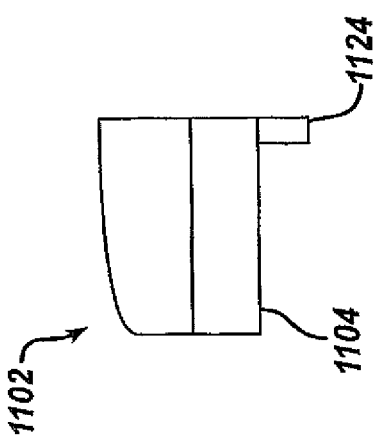
FIG. 34 is a end view of the modular augment glenoid component of FIG. 30.

Referring now to FIG. 32, the locking feature 1120 includes a protrusion 1144 extending outwardly from assembly portion 1142 of the assembly surface 1114 of the second component 1102. The protrusion 1144 is generally rectangular cross-section and includes a length LP, which is substantially greater than its width WP. Referring now to FIGS. 30 and 31, the protrusion 1144 is designed to be matingly fitted with slot 1122 formed in the first component 1102. The slot 1122 is generally rectangular having a width WS, which is substantially smaller than its length LS. Slot 1122 may define arcuate portions 1123 and the protrusion 1144 may likewise have arcuate portions 1145 (see FIG. 32).

Referring to FIGS. 30-33, protrusion of 1144 of the second component 1112 is inserted into the slot 1122 of the first component 1102 to form the locking feature 1120 to secure the second component 1112 to the first component 1102.

The first component 1102 may include a protrusion in the form of a fin 1124 extending from support surface 1104 to secure the first component 1102 to the glenoid fossa 115 of the scapula 116. The fin 1124 may have any suitable shape and may for example have a width WF which is much smaller than the leg LF. The fin 1124 has a generally rectangular cross section.

The first component 1102 may include additional features to secure the first component 1102 to the glenoid fossa 115 of the scapula 116. For example and as is shown in FIGS. 29-34, the first component 1102 may include a pair of spaced apart openings 1132 through which screws 1134 in the form of for example cancellous screws are used to secure the first component 1102 to the glenoid fossa 115 of the scapula 116.

Figure 35:
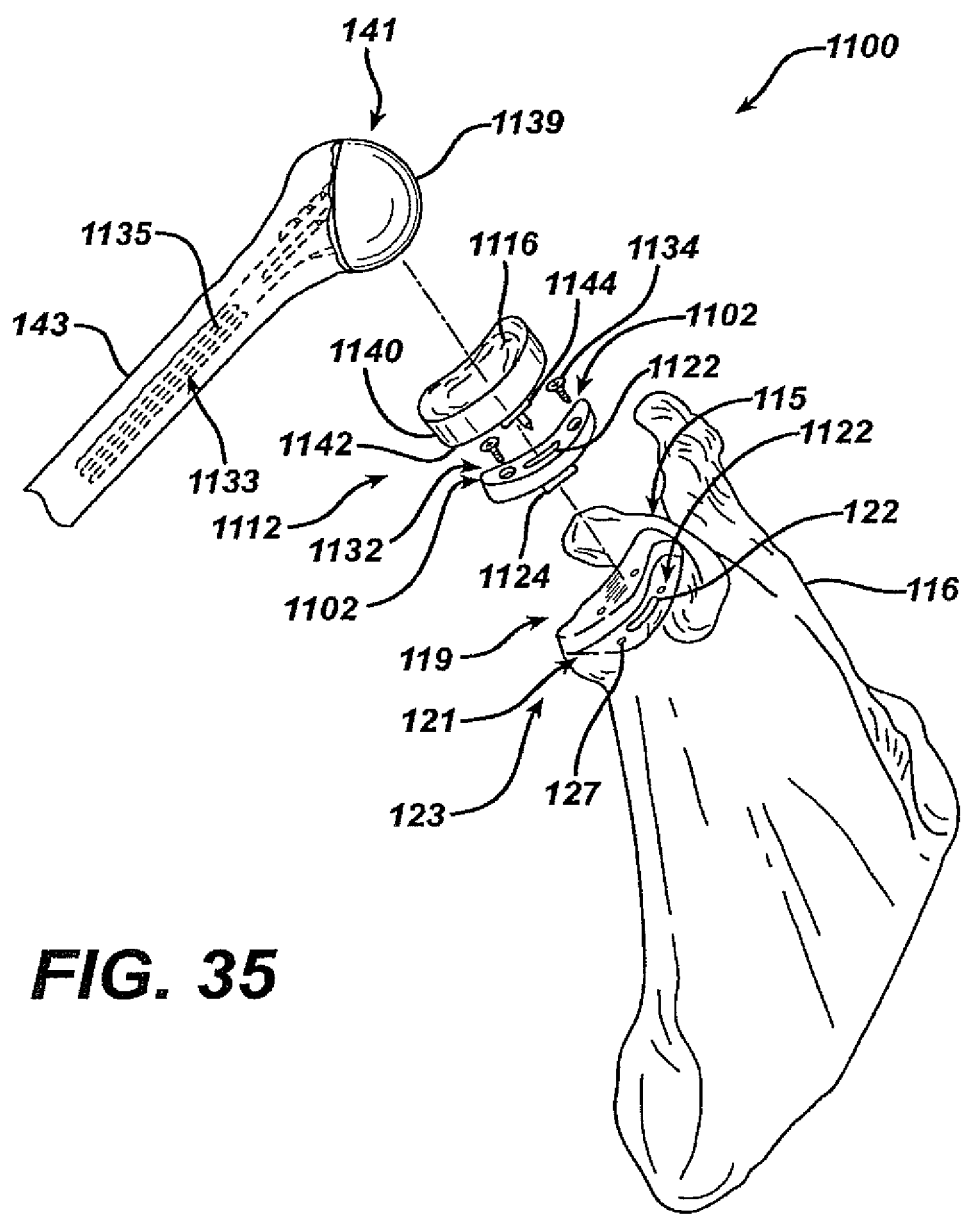
FIG. 35 is an exploded perspective view of glenoid vault of a scapula, a humerus, and the modular augmented glenoid assembly of FIG. 29.

Referring now to FIG. 35, glenoid implant assembly 1100 is shown being assembled onto repaired surface 123 of the scapula 116. The first component 1102 is positioned over and inserted into posterior prepared surface 122. A groove 122 may be prepared in the posterior surface 127. Further, a pair of spaced apart openings 127 may be prepared in the posterior prepared surface 122. The first component 1102 is positioned over and secured to the posterior prepared surface 122. The fin 1124 is positioned in groove 122 and the screws 1134 are positioned through holes 1102 in the first component 1102 and engaged in holes 127 formed in the posterior prepared surface 122.

The second component 1112 is positioned onto the first component 1102 posterioraly and onto anterior prepared surface 119 anteriorly. The protrusion 1144 of the second component 1112 is positioned in groove of 1122 formed in the first component 1102. The articulating surface 1116 of the second component 1112 is designed for cooperation with humeral head 1139 of femoral prosthesis of 1133. The humeral head 1139 extends outwardly from humeral stem 1135 of humeral prosthesis 1133. The humeral stem 1135 is positioned in humeral canal 141 of the humerus 143.

Referring now to FIG. 36 another embodiment of the present invention is shown as surgical method performing surgery 1200. The method 1200 includes a first step 1202 of forming a buttress in a portion of a glenoid surface of a scapula.

The method 1200 further includes a second step 1204 of providing a base glenoid component having a glenoid contacting surface configured to contact the portion of the surface of the glenoid scapula. The base glenoid component also has a connecting surface based from the glenoid contact surface and a buttress surface for cooperation with the buttress shaped recess. The method 1200 further includes a third step 1206 of securing the base glenoid component to the glenoid surface of the scapula such as the glenoid compacting surface is positioned in contact with the glenoid surface of the scapula and the buttress surface is positioned against the buttress shaped recess. The method 1200 further includes a fourth step 1208 of providing a bearing component removeably secured to the base glenoid component the bearing component includes an assembly face and an imposed articulating surface configured to be contacted by the head portion of the humerus. The method 1200 further includes a fifth step 1210 of securing the bearing component to the base glenoid component such that the articulating surfaces positioned to be contacted by the head portion of the humerus and the assembly surface of the bearing component is positioned against the connecting surface of the base glenoid component.

Although the present invention and its advantages have been described in detail, it should be understood that various changes, substitutions, and alterations can be made therein without departing from the spirit and scope of the present invention as defined by the appended claims.

I claim:

1. A method of performing shoulder arthroplasty comprising the steps of:
    forming a buttress-shaped recess in a portion of the patient's glenoid surface of a scapula;
    using a base glenoid component having a glenoid contacting surface configured to contact the portion of the glenoid surface of the patient's scapula, a connecting surface spaced from the glenoid contacting surface, and a buttress surface for cooperation with the buttress-shaped recess, wherein the base glenoid component includes a securing feature;
    securing said base glenoid component to the patient's glenoid surface of the scapula with the securing feature such that the glenoid contacting surface is positioned in contact with the patient's glenoid surface of the scapula, and the buttress surface is positioned against the buttress-shaped recess;
    using a bearing component removably secured to said base glenoid component, said bearing component including an assembly surface thereof and an opposed articulating surface configured to be contacted by the patient's head portion of the humerus, the assembly surface including a mounting surface sized and shaped to cooperate with the patient's glenoid fossa; and
    securing said bearing component to said base glenoid component such that the articulating surface is positioned to be contacted by the patient's head portion of the humerus and a portion of the assembly surface of said bearing component is positioned against the connecting surface of said base glenoid component and the mounting surface extends beyond the connecting surface of said base glenoid component and extends into an anterior position of the patient's scapula.

2. The method of performing shoulder arthroplasty as in claim 1, wherein said forming step includes the step of removing the buttress-shaped recess in the glenoid surface of the scapula with a bone cutter.

3. The method of performing shoulder arthroplasty as in claim 1, wherein said securing feature is an anchoring device.

4. The method of performing shoulder arthroplasty as in claim 1, wherein said forming a buttress-shaped recess step comprises forming a buttress-shaped recess step in a the posterior portion of the glenoid surface of the scapula.

* * * * *